United States Patent
Yancopoulos

(10) Patent No.: US 10,828,345 B2
(45) Date of Patent: *Nov. 10, 2020

(54) USE OF A VEGF ANTAGONIST TO TREAT ANGIOGENIC EYE DISORDERS

(71) Applicant: REGENERON PHARMACEUTICALS, INC., Tarrytown, NY (US)

(72) Inventor: George D. Yancopoulos, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/159,282

(22) Filed: Oct. 12, 2018

(65) Prior Publication Data

US 2019/0046609 A1 Feb. 14, 2019

Related U.S. Application Data

(63) Continuation of application No. 15/471,506, filed on Mar. 28, 2017, now Pat. No. 10,130,681, which is a continuation of application No. 14/972,560, filed on Dec. 17, 2015, now Pat. No. 9,669,069, which is a continuation of application No. 13/940,370, filed on Jul. 12, 2013, now Pat. No. 9,254,338, which is a continuation-in-part of application No. PCT/US2012/020855, filed on Jan. 11, 2012.

(60) Provisional application No. 61/432,245, filed on Jan. 13, 2011, provisional application No. 61/434,836, filed on Jan. 21, 2011, provisional application No. 61/561,957, filed on Nov. 21, 2011.

(51) Int. Cl.
| | | |
|---|---|---|
| A61K 38/17 | (2006.01) | |
| A61K 38/18 | (2006.01) | |
| C07K 14/71 | (2006.01) | |
| C07K 16/22 | (2006.01) | |
| A61K 9/00 | (2006.01) | |
| A61K 39/00 | (2006.01) | |

(52) U.S. Cl.
CPC .......... *A61K 38/179* (2013.01); *A61K 9/0048* (2013.01); *C07K 14/71* (2013.01); *C07K 16/22* (2013.01); *A61K 2039/505* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | |
|---|---|---|
| 7,070,959 B1 | 7/2006 | Papadopoulos |
| 7,303,746 B2 | 12/2007 | Wiegand |
| 7,303,748 B2 | 12/2007 | Wiegand |
| 7,306,799 B2 | 12/2007 | Wiegand |
| 7,396,664 B2 | 7/2008 | Daly et al. |
| 8,092,803 B2 | 1/2012 | Furfine et al. |
| 9,254,338 B2 | 2/2016 | Yancopoulos |
| 9,669,069 B2 | 6/2017 | Yancopoulos |
| 10,130,681 B2 | 11/2018 | Yancopoulos |
| 10,406,226 B2 | 9/2019 | Dix et al. |
| 10,464,992 B2 | 11/2019 | Furfine et al. |
| 2003/0171320 A1 | 9/2003 | Guyer |
| 2005/0163798 A1 | 7/2005 | Papadopoulos et al. |
| 2005/0260203 A1 | 11/2005 | Wiegand et al. |
| 2006/0058234 A1 | 3/2006 | Daly et al. |
| 2006/0172944 A1 | 8/2006 | Wiegand et al. |
| 2007/0190058 A1 | 8/2007 | Shams |
| 2008/0220004 A1 | 9/2008 | Wiegand et al. |
| 2019/0290725 A1 | 9/2019 | Vitti et al. |
| 2019/0388539 A1 | 12/2019 | Dix et al. |
| 2020/0017572 A1 | 1/2020 | Furfine et al. |

FOREIGN PATENT DOCUMENTS

| | | |
|---|---|---|
| JP | 2010-509369 | 3/2010 |
| WO | WO 2000/75319 | 12/2000 |
| WO | WO 2004/106378 A2 | 12/2004 |
| WO | WO 2005/000895 A2 | 1/2005 |
| WO | WO 2006/047325 | 3/2006 |
| WO | WO 2007/022101 A2 | 2/2007 |
| WO | WO 2008/063932 | 5/2008 |
| WO | WO 2012/097019 | 7/2012 |

OTHER PUBLICATIONS

Anonymous "Lucentis (rangibizymab injection) Intravitreal Injection" pp. 103 (Jun. 2006).
Information from ClinicalTrials.gov archive View of NCT00637377 "Vascular Endothelial Growth Factor (VEGF) Trap-Eye: Investigation of Efficacy and Safety in Wet Age-Related Macular Degeneration (AMD) (View 2)" ClinicalTrials.gov. Web. Nov. 30, 2010.
Center for Drug Evaluation and Research Application No. 21-756 Medical Review(s) (Dec. 17, 2004) <URL:https://www.accessdata.fda.gov/drugsatfda_docs/nda/2004/21-756_Macugen_medr.pdf>.
Center for Drug Evaluation and Research BLA Application No. 125156 Medical Review, (Jun. 2006) <URL:https://www.accessdata.fda.gov/drugsatfda_docs/nda/2006/125156s000_Lucentis_MedR.pdf>.

(Continued)

*Primary Examiner* — Christine J Saoud
*Assistant Examiner* — Jon M Lockard
(74) *Attorney, Agent, or Firm* — Thomas Triolo; Karl Bozicevic

(57) ABSTRACT

The present invention provides methods for treating angiogenic eye disorders by sequentially administering multiple doses of a VEGF antagonist to a patient. The methods of the present invention include the administration of multiple doses of a VEGF antagonist to a patient at a frequency of once every 8 or more weeks. The methods of the present invention are useful for the treatment of angiogenic eye disorders such as age related macular degeneration, diabetic retinopathy, diabetic macular edema, central retinal vein occlusion, branch retinal vein occlusion, and corneal neovascularization.

11 Claims, 1 Drawing Sheet

Specification includes a Sequence Listing.

(56) References Cited

OTHER PUBLICATIONS

Charles, Steve (Guest Lecturer) "VEGF Trap Has Positive DME Data" Tenth Annual Retina Fellows Forum Jan. 29 and 30, Chicago, Article Date Mar. 1, 2010.
Dixon et al., "VEGF Trap-Eye for the treatment of neobascular age-related macular degeneration" Expert Opin. Investig. Drugs (2009) 18 (10): 1-8.
Do et al., "An exploratory study of the safety, tolerability and bioactivity of a single intravitreal injection of vascular endothelial growth factor Trap-Eye in patients with diabetic macular oedema" Br J Opthamol. 93(2):144-1449 (Feb. 2009).
Do et al. "The DA VINCI Study: phase 2 primary results of VEGF Trap-Eye in patients with diabetic macular edema" Opthamology 118(9):1819-1826 (Sep. 2011).
The Eyetech Study Group, "Anti-Vascular Endothelial Growth Factor Therapy for Subfoveal Choroidal Neovascularization Secondary to Age-related Macular Degeneration" American Academy of Ophthamology, 110(5):979-986 (May 2003).
HEIERet al., "rhuFab V2 (anti-VEGF Antibody) for Treatment of Exudative AMD" Symposium 8:Experimental and Emerging Treatments for Choroidal Neovascularization, 10 pp (2002).
Heier et al., "RhuFab V2 in Wet AMD—6 Month Continued Improvement Following Multiple Intravitreal Injections" Invest Ophthalmol Vis Sci, 44:E-Abstract 972 (2003).
Heier et al., "Intravitreal Aflibercept (VEGF Trap-Eye) in Wet Age-related macular Degeneration," Ophthalmology, 119:2537-2548 (2012).
Information from ClinicalTrials.gov archive on the VIEW 2 study (NCT00637377) "VEGF Trap-Eye: Investigation of Efficacy and Safety in Wet AMD (VIEW 2)" version available and updated on Mar. 17, 2008.
Information from ClinicalTrials.gov archive on the view of NCT00509795 "Vascular Endothelial Growth Factor (VEGF) Trap-Eye: Investigation of Efficacy and Safety in Wet Age-Related Macular Degeneration (AMD)" (Dec. 1, 2009).
Information from ClinicalTrials.gov archive on the view of NCT00789477 "DME and VEGF Trap-Eye: Investigation of Clinical Impact" (Nov. 18, 2010).
Information from ClinicalTrials.gov archive on the view of NCT00509795 "Vascular Endothelial Growth Factor (VEGF) Trap-Eye: Investigation of Efficacy and Safety in Wet Age-Related Macular Degeneration (AMD)" (Jan. 7, 2011).
Krzystolik et al., "Prevention of Experimental Choroidal NEovascularization With Intravitreal Anti-Vascular Endothelial Growth Factor Antibody Fragment" Arch Ophthalmol., 120:338-346 (Mar. 2002).
Mitra et al., "Review of anti-vascular endothelial growth factor therapy in macular edema secondary to central retinal vein occlusions" Expert Review in Ophthalmo, Taylor & Francis, GB (Jan. 1, 2011) 6(6):623-629.
Mousa and Mousa, "Current Status of Vascular Endothelial Growth Factor Inhibition in Age-Related Macular Degeneration" Biodrugs 2010; 24(3); 183-194.
Nguyen et al., "A Phase I Study of Intravitreal Vascular Endothelial Growth Factor Trap-Eye in Patients with Neovascular Age-Related Macular Degeneration" Opthamology, J.B. Lippincott Co., Philadelphia, PA, US, 116(11):2141-2148 (Nov. 1, 2009) 116(11):2141-2148 (Nov. 1, 2009).
Nguyen et al., "A phase I trial of an IV-administered vascular endothelial growth factor trap for treatment in patients with choroidal neovascularization due to age-related macular degeneration" Ophthalmology (Sep. 2006) 113(9):1522e1-1522e14 (epub Jul. 28, 2006).
Nichols, Earl R., "AAO: Ranibizumab (rhuRab) May Improve Vision in Age-Related Macular Degeneration" Doctor's Guide Global Edition, www.pslgroup.com/dg/23f2aa.htm, pp. 1-2 (Nov. 24, 20013).

Olivera et al., "VEGF Trap R1R2 suppresses experimental corneal angiogenesis" European Journal of Ophthalmology (Jan. 1, 2010) 20(1):48-54.
Pai et al., "Current concepts in intravitreal drug therapy for diabetic retinopathy" Saudi Journal of Opthamology 24(4):143-149 (Jun. 30, 2010).
Regeneron Pharmaceuticals, Inc. Form 10-Q, published on Nov. 7, 2007 for the period ending Sep. 30, 2007.
Regeneron, Press release "Regeneron Reports First Quarter 2008 Financial and Operating Results", May 1, 2008.
Regeneron Press Release "Bayer and Regeneron Report Positive Top-Line Results of Two Phase 3 Studies with VEGF Trap-Eye in Wet Age-related Macular Degeneration" Nov. 22, 2010.
Regeneron Press Release "Regeneron and Bayer Report Positive Results for VEGF Trap-Eye in Phase 3 Study in Central Retinal Vein Occlusion (CRVO) and in Phase 2 Study in Diabetic Macular Edema (DME)" Dec. 20, 2010.
Regeneron Pharmaceuticals Inc., "VEGF Trap-Eye Final Phase 2 Results in Age-related Macular Degeneration Presented at 2008 Retina Society Meeting" (Sep. 28, 2008) (XP-002770952).
Simo and Hernandez, "Advances in Medical Treatment of Diabetic Retinopathy" Diabetes Care, vol. 32, No. 8, Aug. 2009.
Slides for the 2008 Retina Society Meeting "VEGF Trap-Eye in Wet AMD CLEAR-IT 2: Summary of One-Year Key Results", Sep. 28, 2008.
Stewart, "THe expanding role of vascular endothelial growth factor inhibitors in opthamology" Mayo Clin Proc. 87(1):77-88 (Jan. 2012).
Thomas Reuters Integrity "VEGF Trap-Eye final phase II results in age-related macular degeneration presented at 2008 Retina Society Meeting" (Sep. 28, 2008).
WHO Drug Information, "International Nonproprietary Names for Pharmaceutical Substances (INN)" vol. 20, No. 2, 2006, pp. 115-119.
Barbazetto, "Dosing Regimen and the Frequency of Macular Hemorrhages in Neovascular Age-Related Macular Degeneration Treated With Ranibizumab." Retina, 30:9, 1376-85, 2010.
Bayer Investor News, "Bayer and Regeneron Start additional Phase 3 Study for VEGF Trap=Eye in Wet Age-related Macular Degeneration." May 8, 2008.
Boyer, "A Phase IIIb Study to Evaluate the Safety of Ranibizumab in Subjects with Neovascular Age-related Macular Degeneration." Opthalmology, 116:9, 1731-39, Sep. 2009.
Brown, "Ranibizumab versus Verteporfin for Neovascular Age-Related Macular Degeneration." N Engl J Med 355:14, 1432-44, Oct. 5, 2006.
Brown, "Primary Endpoint Results of a Phase II Study of Vascular Endothelial Growth Factor Trap-Eye in Wet Age-related Macular Degeneration." Ophthalmology, 118:6, 1089-97, Jun. 2011.
Brown, "Long-term Outcomes of Ranibizumab Therapy for Diabetic Macular Edema: The 36-Month Results from Two phase III Trials." Ophthalmology, 2013.
Campochiaro, "Ranibizumab for Macular Edema following Branch Retinal Vein Occlusion." Ophthalmology, 2010.
Campochiaro, "Sustained Benefits from Ranibizumab for Macular Edema following Central Retinal Vein Occlusion: Twelve-Month Outcomes of a phase III Study." Ophthalmology, 188:10, 2041-49, Oct. 2011.
Csaky, "Safety Implications of Vascular Endothelial Growh Factor Blockade for Subjects Receiving Intravitreal Anti-Vascular Endothelial Growth Factor Therapies." Am. J. Opthalmology, 148:5, 647-56, Nov. 2009.
Do, "One-Year Outcomes of the DA VINCI Study of VEGF Trap-Eye in Eyes with Diabetic Macular Edema." Ophthalmology, 2012.
Engelbert, "The 'Treat and Extend' Dosing Regimen of Intravitreal Anti-Vascular Endothelial Growth Factor Therapy for Neovascular Age-Related Macular Degeneration." Ophthalmology Management, Jun. 2010, available at http://www.visioncareprofessional.com/emails/amdupdate/index.asp?issue=42.
Engelbert, "Long-Term Follow-Up for Type 1 (Subretinal Pigment Epithelium) Neovascularization Using a Modified 'Treat and Extend'

(56) References Cited

OTHER PUBLICATIONS

Dosing Regiment of Intravitreal Antivascular Endothelial Growth Factor Therapy." Retina, 30:9, 1368-75, 2010.
Engelbert, "'Treat and Extend' Dosing of Intravitreal Antivascular Endothelial Growth Factor Therapy for Type 3 Neovascularization/ Retinal Angiomatous Proliferation." Retina, 29:10, 1424-31, 2009.
Eylea®, Highlights of Prescribing Information, Revised Aug. 2018.
Fung, "An Optical Coherence Tomography-Guided, Variable Dosing Regiment with Intravitreal Ranibizumab (Lucentis) for Neovascular Age-related Macular Degeneration." Am J Ophthalmology 143:4, 566-83, Apr. 2007.
Gale, "Complementary and Coordinated Roles of the VEGFs and Angiopoietins during Normal and Pathologic Vascular Formation." Cold Spring Harbor Symposia on Quantitative Biology, vol. LXVIL, pp. 267-73, 2002.
Garcia-Quintanilla, "Pharmacokinetics of Intravitreal Anti-VEGF Drugs in Age-Related Macular Degeneration." Pharmaceutics, 11:365, 2019.
Gomez-Manzano, "VEGF Trap induces antiglioma effect at different stages of disease." Society for Neuro-Oncology, Dec. 2008.
Gragoudas, "Pegaptanib for Neovascular Age-Related Macular Degeneration." N Engl J Med 351:27, 2805-16, Dec. 30, 2004.
Heier, "Intravitreal Aflibercept for Diabetic Macular Edema." Ophthalmology, 2016.
Ho et al., Slides entitled CLEAR IT 2 One-Year Key Results, Retina Society 2008.
Korobelnik, "Intravitreal Aflibercept for Diabetic Macular Edema." Ophthalmology, 121:11, 2247-54, Nov. 2014.
Lalwani, "All About PrONTO: Study Yielded Good Results in AMD With Treatment Guided by OCT." Retina Today, May 2007.
Lalwani, A Variable-dosing Regimen with Intravitreal Ranibizumab for Neovascular Age-related Macular Degeneration: Year 2 of the PrONTO Study. Am J Ophthalmology, 148:1, 43-58, Jul. 2009.
Levine, "Macular Hemorrhage in Neovascular Age-Related Macular Degeneration After Stabilization With Antiangiogenic Therapy." Retina, 29:8, 1074-79, 2009.
Margolis, "Hemorrhagic Recurrence of Neovascular Age-Related Macular Degeneration Not Predicted by Spectral Domain Optical Coherence Tomography." Retinal Cases & Brief Reports, 4:1, 2010.
Massin, "Safety and Efficacy of Ranibizumab in Diabetic Macular Edema (RESOLVE Study*)." Diabetes Care, 33:11, 2399-405, Nov. 2010.
Mitchell, "The RESTORE Study, Ranibizumab Monotherapy or Combined with Laser versus Laser Monotherapy for Diabetic Macular Edema." Ophthalmology, 188:4, 615-25, Apr. 2011.
Nguyen, "Ranibizumab for Diabetic Macular Edema, Results from 2 Phase III Randomized Trials: RISE and RIDE." Ophthalmology, 119:4, 789-801, Apr. 2012.
Regeneron Press Release, "Bayer and Regeneron Dose First Patient in Second Phase 3 Study for VEGF Trap-Eye in Wet Age-Related Macular Degeneration." May 8, 2008.
Regeneron Press Release, "VEGF Trap-Eye Shows Positive Results in a Phase 2 Study in Patients With Diabetic Macular Edema." Feb. 18, 2010.
Rosenfeld, "Ranibizumab for Neovascular Age-Related Macular Degeneration." N Engl J Med, 355:14, 1419-31, Oct. 5, 2006.
Rosenfeld, "Lessons Learned From Avastin and OCT-The Great, the Good, the Bad, and the Ugly: The LXXV Edward Jackson Memorial Lecture." Am. J. Ophthalmology, 204:26-45, Aug. 2019.
Schmidt-Erfurth, "Efficacy and Safety of Monthly versus Quarterly Ranibizumab Treatment in Neovascular Age-related Macular Degeneration." Ophthalmology, 2010.
Schmidt-Erfurth, "Three-Year Outcomes of Individualized Ranibizumab Treatment in Patients with Diabetic Macular Edema." Ophthalmology, 121:5, 1045-53, May 2014.
Spaide, "Ranibizumab According to Need: A Treatment for Age-related Macular Degeneration." Am J Ophthalmology, Apr. 2007.
Wolfson, "Regeneron Focuses on Age-Related Macular Degeneration." Chemistry & Biology 15:303-304, Apr. 2008.

Yancopoulos, "Vascular-specific growth factors and blood vessel formation." Nature 407:242-48, Sep. 14, 2000.
Yancopoulos, "Clinical Application of Therapies Targeting VEGF." Cell 143, Oct. 1, 2010.
Yung, "moving Toward the Next Steps in Angiogenesis Therapy?" Society for Neuro-Oncology, 10:939, 2008.
Browning et al. "Aflibercept for age-related macular degeneration: a game-changer or quiet addition?" American Journal of Ophthalmology, vol. 154(2):222-226 (Aug. 1, 2012).
Campochiaro et al. "Ranibizumab for Macular Edema Due to Retinal Vein Occlusions Implication of VEGF as a Critical Stimulator" Molecular Therapy, 16(4):791-799 (2008).
Cao, "A Subretinal Matrigel Rat Choroidal Neovascularization (CNV) Model and Inhibition of CNV and Associated Inflammation and Fibrosis by VEGF Trap" Investigative Ophthalmology & Visual Science, 51(11):6009-6017 (Nov. 2010).
Eichten, "Rapid decrease in tumor perfusion following VEGF blockade predicts long-term tumor growth inhibition in preclinical tumor models" Angiogenesis, 16:429-441 (2013).
Ho, "VEGF Trap-Eye in Wet AMD—CLEAR-IT 2: One-Year OCT and FA Outcomes" CLEAR-IT 2 Study Group, pp. 1-24 (Sep. 28, 2008).
Holash, "VEGF-Trap: A VEGF blocker with potent antitumor effects" PNAS 99(17)11393-11398 (Aug. 20, 2002).
Holash, "Inhibitors of growth factor receptors, signaling pathways and angiogenesis as therapeutic molecular agents." Cancer Metastasis 25:243-252 (2006).
Karia, Niral, "Retinal vein occlusion: pathophysiology and treatment options" Clinical Ophthalmology, 4:809-816 (2010).
Kuo, "Comparative evaluation of the antitumor activity of antiangiogenic proteins delivered by gene transfer" PNAS 98(8):4605-4610 (Apr. 10, 2001).
Lucentis Label Title, 7 pages, Jun. 30, 2010 [Cited in Third Party Observations filed in parent U.S. Appl. No. 16/055,847].
Ohr, "Aflibercept in wet age-related macular degeneration: a perspective review" Ther. Adv. Chronic Dis., 3(4):153-161 (2012).
Papadppoulos, "Binding and neutralization of vascular endothelial growth factor (VEGF) and related ligands by VEGF Trap, ranibizumab and bevacizumab" Angiogenesis, 15:171-185 (2012).
Regillo et al., "Randomized, Double-Masked, Sham-Controlled Trial of Ranibizumab for Neovascular Age-related Macular Degeneration: OIER Study Year 1" American Journal of Ophthalmology, 145(2):239-248 (2008).
Schnichels, "Comparative toxicity and proliferation testing of aflibercept, bevacizumab and ranibizumab on different ocular cells." Br. J. Opthalmol. (May 17, 2013).
Sharma and S. and Kaiser, P. K., Update on VEGF TRAP-Eye Clinical Trials and Retinal. Physician, Nov./Dec. 2010, p. 1-6, <URL: https://www.retinalphysician.com/issues/2010/nov-dec/update-on-vegf-trap-eye-clinical-trials>.
Stewart et al., "Predicted biological activity of intravitreal VEGF Trap" British Journal of Ophthalmology, 2008, vol. 92, No. 5, p. 667-668.
Stewart, "Aflibercept" Nature Reviews: Drug Discovery 11:269-270 (Apr. 1, 2012).
Thurston, "Vascular endothelial growth factor and other signaling pathways in developmental and pathologic angiogenesis." International Journal of Hematology 80:7-20 (2004).
Wachsberger, "VEGF trap in combination with radiotherapy improves tumor control in u87 glioblastoma." Int. J. Radiation Oncology Biol Phys. 67(5):1526-1537 (2007).
ADSIS R&D Profile "Aflibercept: AVE 0005, AVE 005, AVE0005, VEGF Trap—Regeneron, VEGF Trap (R1R2), VEGF Trap-Eye." Drugs R D, 9(4):261-269 (2008).
N/A "Materials from Jun. 2011 FDA Committee Mtg" (Jun. 17, 2011).
N/A "Materials from Dec. 2011 FDA Committee Mtg" (Dec. 1, 2011).
Vascular Endothelial Growth Factor Trap‐ Eye Investigation of Efficacy and Safety in Central Retinal Vein Occlusion title, 8 pages, Nov. 12, 2009, US [Cited in Third Party Observations filed in parent U.S. Appl. No. 16/055,847].

(56) References Cited

OTHER PUBLICATIONS

U.S. Appl. No. 16/055,847—Third Party Submissions dated May 1, 2019.
Brown, "Long-term Outcomes of Ranibizumab Therapy for Diabetic Macular Edema: The 36-Month Results from Two phase III Trials." Ophthalmology, 120(10):2013-22 (Oct. 2013).
Campochiaro, "Ranibizumab for Macular Edema following Branch Retinal Vein Occlusion: six-month primary end point results of a phase III study." Ophthalmology, 117(6):1102-1112 (Jun. 2010).
Dixon et al., "VEGF Trap-Eye for the treatment of neovascular age-related macular degeneration" Expert Opin. Investig. Drugs, 18(10):1573-1580 (2009).
Do, "One-Year Outcomes of the DA VINCI Study of VEGF Trap-Eye in Eyes with Diabetic Macular Edema." Ophthalmology, 119(8):1658-65 (2012).
Engelbert, "The 'Treat and Extend' Dosing Regimen of Intravitreal Anti-Vascular Endothelial Growth Factor Therapy for Neovascular Age-Related Macular Degeneration." Ophthalmology Management, Issue 42, (Jun. 2010) available at http://visioncareprofessional.com/emails/amdupdate/index.asp?issue=42.
Gomez-Manzano, "VEGF Trap induces antiglioma effect at different stages of disease." Neuro-Oncology, 10:940-945 (Dec. 2008).
Heier, "Intravitreal Aflibercept for Diabetic Macular Edema: 148-Week Results from the VISTA and VIVID Studies." Ophthalmology, 123(11):2376-2385 (Nov. 2016).
Information from ClinicalTrials.gov archive on the view of NCT01012973 Vascular Endothelial Growth Factor (VEGF) Trap-Eye: Investigation of Efficacy and Safety in Central Retinal Vein Occlusion (CRVO)(GALILEO) 7 pages, first posted Nov. 13, 2009; results first posted Nov. 22, 2012; last update posted Nov. 3, 2014; printed Dec. 4, 2019 (https://clinicaltrials.gov/ct2/show/study/NCT01012973) (Note: May correspond to "Vascular Endothelial Growth Factor Trap‐ Eye Investigation of Efficacy and Safety in Central Retinal Vein Occlusion title, 8 pages, Nov. 12, 2009, US [Cited in Third Party Observations filed in parent U.S. Appl. No. 16/055,847]" which was cited in the Third Party Observations dated May 1, 2019).
Kaiser, "Vascular endothelial growth factor Trap-Eye for diabetic macular oedema." Br. J. Ophthalmol, 93(2):135-36 (Feb. 2009).
Margolis, "Hemorrhagic Recurrence of Neovascular Age-Related Macular Degeneration Not Predicted by Spectral Domain Optical Coherence Tomography." Retinal Cases & Brief Reports, 4:1-4 (2010).
Nichols, Earl R., "AAO: Ranibizumab (rhuRab) May Improve Vision in Age-Related Macular Degeneration" Doctor's Guide Global Edition, www.pslgroup.com/dg/23f2aa.htm, pp. 1-2 (Nov. 24, 2003).
Schmidt-Erfurth, "Efficacy and Safety of Monthly versus Quarterly Ranibizumab Treatment in Neovascular Age-related Macular Degeneration: The EXCIE Study" Ophthalmology, 118(5)831-839 (2010).
Schnichels, "Comparative toxicity and proliferation testing of aflibercept, bevacizumab and ranibizumab on different ocular cells." Br. J. Ophthalmol., 97:917-923 (2013).
Simo and Hernandez, "Advances in Medical Treatment of Diabetic Retinopathy" Diabetes Care, 32(8):1556-1562 (Aug. 2009).
Spaide, "Ranibizumab According to Need: A Treatment for Age-related Macular Degeneration." Am J Ophthalmology, 143(4):679-680 (Apr. 2007).
Vascular Endothelial Growth Factor Trap‐ Eye Investigation of Efficacy and Safety in Central Retinal Vein Occlusion title, 8 pages, Nov. 12, 2009, US [Cited in Third Party Observations filed in parent U.S. Appl. No. 16/055,847] Note: May correspond to Information from ClinicalTrials.gov archive on the view of NCT01012973 "Vascular Endothelial Growth Factor (VEGF) Trap-Eye: Investigation of Efficacy and Safety in Central Retinal Vein Occlusion (CRVO)(GALILEO) 7 pages, first posted Nov. 13, 2009; results first posted Nov. 22, 2012; last update posted Nov. 3, 2014; printed Dec. 4, 2019 (https://clinicaltrials.gov/ct2/show/study/NCT01012973)" Office Action dated Dec. 10, 2019 in U.S. Appl. No. 16/055,847.
Yancopoulos, "Clinical Application of Therapies Targeting VEGF." Cell 143:13-16 (Oct. 1, 2010).
Gutierrez et al., "Intravitreal bevacizumab (Avastin) in the treatment of macular edema secondary to retinal vein occlusion" Clin. Ophthalmol., 2(4):787,791 (2008).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 38 pages, Latest version submitted Oct. 27, 2014 on ClinicalTrials.gov (NCT01012973_01182013_27424.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov(NCT01012973_01252011_27433.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 11 pages, Latest version submitted Oct. 27, 2014 on ClinicalTrials.gov(NCT01012973_01262012_27428.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 38 pages, Latest version submitted Oct. 27, 2014 on ClinicalTrials.gov (NCT01012973_01302013_27423.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 12 pages, Latest version submitted Oct. 27, 2014 on ClinicalTrials.gov (NCT01012973_02092010_27442.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 11 pages, Latest version submitted Oct. 27, 2014 on ClinicalTrials.gov (NCT01012973_02202012_27427.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 12 pages, Latest version submitted Oct. 27, 2014 on ClinicalTrials.gov (NCT01012973_03162010_27441.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov (NCT01012973_04082011_27432.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 12 pages, Latest version submitted Oct. 27, 2014 on ClinicalTrials.gov (NCT01012973_04162010_27440.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov (NCT01012973_06232011_27431.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 12 pages, Latest version submitted Oct. 27, 2014 on ClinicalTrials.gov (NCT01012973_07222010_27439.1).
Updated Information from ClinicalTrials.gov archive History of Changes for Study: NCT01012973 Vascular Endothelial Growth

(56) References Cited

OTHER PUBLICATIONS

Factor (VEGF) Trap-Eye: Investigation of Efficacy and Safety in Central Retinal Vein Occlusion (CRVO)(GALILEO) 12 pages, Latest version submitted Oct. 27, 2014 on ClinicalTrials.gov (NCT01012973_08252010_27438.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov (NCT01012973_08262010_27437.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov (NCT01012973_09082010_27436.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov (NCT01012973_09192011_27430.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov (NCT01012973_10042010_27435.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 38 pages, Latest version submitted Oct. 27, 2014 on ClinicalTrials.gov (NCT01012973_10232012_27426.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 38 pages, Latest version submitted Oct. 27, 2014 on ClinicalTrials.gov (NCT01012973_10272013_27422.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov (NCT01012973_11012010_27434.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 12 pages, Latest version submitted Oct. 27, 2014 on ClinicalTrials.gov (NCT01012973_11132009_27444.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 10 pages, Latest version submitted Oct. 27, 2014 on ClinicalTrials.gov (NCT01012973_11292011_27429.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 38 pages, Latest version submitted Oct. 27, 2014 on ClinicalTrials.gov (NCT01012973_12182012_27425.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(GALILEO) 12 pages, Latest version submitted Oct. 27, 2014 on ClinicalTrials.gov (NCT01012973_12212010_27443.1).
Anonymous "Anti-VEGF 2019: The State of the Art" Review of Ophthalmology (published Aug. 5, 2019).
Chatziralli et al. "Intravitreal aflibercept for neovascular age-related macular degeneration in patients aged 90 years or older: 2-year visual acuity outcomes" Eye (2018) 32:1523-1529.
Chung et al. "Ziv-aflibercept: A novel angiogenesis inhibitor for the treatment of metastatic colorectal cancer" Am J Heath-Syst Pharm (Nov. 1, 2013) 70:1887-1896.
Cooper et al., "Increased Renal Expression of Vascular Endothelial Growth Factor (VEGF) and Its Receptor VEGFR-2 in Experimental Diabetes" Diabetes (1999) 48:22292239.
Croll et al., "VEGF-mediated inflammation precedes angiogenesis in adult brain" Experimental Neurology (2004) 187:388-402.
DeVRIESE et al., "Antibodies against Vascular Endothelial Growth Factor Improve Early Renal Dysfunction in Experimental Diabetes" J. Am. Soc. Nephrol (2001) 12:993-1000.
Eremina et al., "Glomerular-specific alterations of VEGF-A expression lead to distinct congenital and acquired renal diseases" Journal of Clinical Investigation (Mar. 2003) 111(5):707-716.
Eriksson et al., "Structure, Expression and Receptor-Binding Properties of Novel Vascular Endothelial Growth Factors" Vascular Growth Factors and Angiogenesis, Springer (1999) pp. 41-57.
Ferrara, N. "Vascular Endothelial Growth Factor: Molecular and Biological Aspects" Advances in Organ Biology (1999) pp. 1-30.
Ferrara et al., "Clinical applications of angiogenic growth factors and their inhibitors" Nature Medicine (Dec. 1999) 5(12):1359-1364.
Flyvbjerg et al., "Amelioration of Long-Term Renal Changes in Obese Type 2 Diabetic Mice by a Neutralizing Vascular Endothelial Growth Factor Antibody" Diabetes (Oct. 2002) 51:3090-3094.
Holash et al., "Vessel Cooption, Regression, and Growth in Tumors Mediated by Angiopoietins and Vegf" Science (Jun. 18, 1999) 284(5422):1994-1998.
Korobelnik et al., "Intravitreal Aflibercept Injection for Macular Edema Resulting from Central Retinal Vein Occlusion" American Academy of Ophthalmology (2014) 121(1):202208.
Mitchell, Edith P. "Targeted Therapy for Metastatic Colorectal Cancer: Role of Aflibercept" Clinical Colorectal Cancer (2013) 12(2):73-85.
Noguera-Troise et al., "Blockade of D114 inhibits tumour growth by promoting nonproductive angiogenesis" Nature (Dec. 2006) 444:1032-1037.
Rudge et al., "VEGF Trap complex formation measures production rates of VEGF, providing a biomarker for predicting efficacious angiogenic blockade" PNAS (Nov. 20, 2007) 104(47):18363-18370.
Schmidt-Erfurth et al., "Intravitreal Aflibercept Injection for Neovascular Age-related Macular Degeneration" Ophthalmology (2014) 121:193-201.
Semeraro et al., "Aflibercept in wet AMD: specific role and optimal use" Drug Design, Development and Therapy (Aug. 2, 2013) 7:711-722.
Tannock et al., "Aflibercept versus placebo in combination with docetaxel and prednisone for treatment of men with metastatic castration-resistant prostate cancer (VENICE): a phase 3, double-blind randomized trial" Lancet Oncol (2013) 14:760-768.
Thurston, Gavin "Complementary actions of VEGF and Angiopoietin-1 on blood vessel growth and leakage" J. Anat. (2002) 200:575-580.
Xia et al., "Transgenic delivery of VEGF to mouse skin leads to an inflammatory condition resembling human psoriasis" Blood (Jul. 1, 2003) 102(1):161-168.
Benz et al. "CLEAR-IT-2: Interim Results of the Phase II, Randomized, Controlled Dose-and Interval-ranging Study of Repeated Intravitreal VEGF Trap Administration in Patients With Neovascular Age-related Macular Degeneration (AMD)" ARVO Annual Meeting Abstract (May 2007).
Do et al. "Results of a Phase 1 Study of Intravitreal VEGF Trap in Subjects with Diabetic Macular Edema: The CLEAR-IT DME Study" ARVO Annual Meeting Abstract (May 2007).

(56) References Cited

OTHER PUBLICATIONS

Do et al. "VEGF Trap-Eye Vision-specific Quality of Life through 52 Weeks in Patients with Neovascular AMD in CLEAR-IT 2: A Phase 2 Clinical Trial" ARVO Annual Meeting Abstract (Apr. 2009).
Haller et al., "VEGF Trap-Eye in CRVO: Primary Endpoint Results of the Phase 3 Copernicus Study" ARVO Annual Meeting Abstract (Apr. 2011).
Heier et al., "CLEAR-IT 2: Phase 2, Randomized Controlled Dose and Interval-Ranging Study of Intravitreal VEFG Trap Eye in Patients with Neovascular Age-Related Macular Degeneration: Predictive Factors for Visual Acuity" ARVO Annual Meeting Abstract (Apr. 2009).
Heier et al., "The 1-year Results of Clear-It 2, a Phase 2 Study of Vascular Endothelial Growth Factor Trap-Eye Dosed As-needed After 12-week Fixed Dosing" Ophthalmology 2011;118:1098-1106 (Jun. 2011).
Heier et al., "The 1-year Results of CLEAR-IT 2, a Phase 2 Study of Vascular Endothelial Growth Factor Trap-Eye Dosed As-needed After 12-week Fixed Dosing: Erratum" Ophthalmology 2011;118:1700 (Sep. 2011).
Information from ClinicalTrials.gov archive History of Changes for Study: NCT00320775 "Safety and Tolerability of Intravitreal Administration of VEGF Trap in Patients With Neovascular Age-Related Macular Degeneration" 70 pages, Latest version submitted Jun. 8, 2011 on ClinicalTrials.gov (NCT00320775_2006-2011).
Information from ClinicalTrials.gov archive History of Changes for Study: NCT00320775 "Safety and Tolerability of Intravitreal Administration of Vegf Trap in Patients With Neovascular Age-Related Macular Degeneration" 10 pages, Latest version submitted Mar. 16, 2015 on ClinicalTrials.gov (NCT00320775_2015).
Information from ClinicalTrials.gov archive History of Changes for Study: NCT00320788 "Safety and Efficacy of Repeated Intravitreal Administration of Vascular Endothelial Growth Factor (VEGF) Trap in Patients With Wet Age-Related Macular Degeneration (AMD)" 71 pages, Latest version submitted Dec. 1, 2011 on ClinicalTrials.gov (NCT00320788_2006-2011).
Information from ClinicalTrials.gov archive History of Changes for Study: NCT00320788 "Safety and Efficacy of Repeated Intravitreal Administration of Vascular Endothelial Growth Factor (VEGF) Trap in Patients With Wet Age-Related Macular Degeneration (AMD)" 31 pages, Latest version submitted Jan. 27, 2012 on ClinicalTrials.gov (NCT00320788_2012).
Information from ClinicalTrials.gov archive History of Changes for Study: NCT00320814 "Phase 1 Study of VEGF Trap in Patients With Diabetic Macular Edema" 30 pages, Latest version submitted Jun. 8, 2011 on ClinicalTrials.gov (NCT00320814_2006-2011).
Information from ClinicalTrials.gov archive History of Changes for Study: NCT00509795 "Double-Masked Study of Efficacy and Safety of IVT VEGF Trap-Eye in Subjects With Wet AMD (VIEW 1)" 318 pages, Latest version submitted Dec. 1, 2011 on ClinicalTrials.gov (NCT00509795_2007-2011).
Information from ClinicalTrials.gov archive History of Changes for Study: NCT00509795 "Double-Masked Study of Efficacy and Safety of IVT VEGF Trap-Eye in Subjects With Wet AMD (VIEW 1)" 200 pages, Latest version submitted Dec. 20, 2012 on ClinicalTrials.gov (NCT00509795_2012).
Information from ClinicalTrials.gov archive History of Changes for Study: NCT00527423 "Randomized, Single-Masked, Long-Term, Safety and Tolerability Study of VEGF Trap-Eye in AMD" 64 pages, Latest version submitted Nov. 1, 2011 on ClinicalTrials.gov (NCT00527423_2007-2011).
Information from ClinicalTrials.gov archive History of Changes for Study: NCT00527423 "Randomized, Single-Masked, Long-Term, Safety and Tolerability Study of VEGF Trap-Eye in AMD" 42 pages, Latest version submitted Jun. 10, 2013 on ClinicalTrials.gov (NCT00527423_2012-2013).
Information from ClinicalTrials.gov archive History of Changes for Study: NCT00637377 "Vascular Endothelial Growth Factor (VEGF) Trap-Eye: Investigation of Efficacy and Safety in Wet Age-Related Macular Degeneration (AMD) (VIEW 2)" 667 pages, Latest version submitted Dec. 16, 2011 on ClinicalTrials.gov (NCT00637377_2008-2011).
Information from ClinicalTrials.gov archive History of Changes for Study: NCT00637377 "Vascular Endothelial Growth Factor (VEGF) Trap-Eye: Investigation of Efficacy and Safety in Wet Age-Related Macular Degeneration (AMD) (VIEW 2)" 289 pages, Latest version submitted Nov. 28, 2014 on ClinicalTrials.gov (NCT00637377_2012-2014).
Information from ClinicalTrials.gov archive History of Changes for Study: NCT00789477 "DME and VEGF Trap-Eye [Intravitreal Aflibercept Injection (IAI;EYLEA®;BAY86-5321)] INvestigation of Clinical Impact (DA VINCI)" 135 pages, Latest version submitted May 2, 2011 on ClinicalTrials.gov (NCT00789477_2008-2011).
Information from ClinicalTrials.gov archive History of Changes for Study: NCT00789477 "DME and VEGF Trap-Eye [Intravitreal Aflibercept Injection (IAI;EYLEA®BAY86-5321)] INvestigation of Clinical Impact (DA VINCI)" 53 pages, Latest version submitted Aug. 28, 2014 on ClinicalTrials.gov (NCT00789477_2013-2014).
Information from ClinicalTrials.gov archive History of Changes for Study: NCT00943072 "Vascular Endothelial Growth Factor (VEGF) Trap-Eye: Investigation of Efficacy and Safety in Central Retinal Vein Occlusion (CRVO)" 98 pages, Latest version submitted May 9, 2011 on ClinicalTrials.gov (NCT00943072_2009-2011).
Information from ClinicalTrials.gov archive History of Changes for Study: NCT00943072 "Vascular Endothelial Growth Factor (VEGF) Trap-Eye: Investigation of Efficacy and Safety in Central Retinal Vein Occlusion (CRVO)" 64 pages, Latest version submitted Apr. 16, 2013 on ClinicalTrials.gov (NCT00943072_2012-2013).
Major et al., "DA VINCI: DME and VEGF Trap-Eye: Investigation of Clinical Impact: Phase 2 Study in Patients with Diabetic Macular Edema (DME)" ARVO Annual Meeting Abstract (Apr. 2010).
Nguyen et al., "Randomized, Double-masked, Active-controlled Phase 3 Trial of the Efficacy and Safety of Intravitreal VEGF Trap-Eye in Wet AMD: One-year Results of the View 1 Study" ARVO Annual Meeting Abstract (Apr. 2011).
Nguyen et al., "Results of a Phase I, Dose-Escalation, Safety, Tolerability, and Bioactivity Study of Intravitreous VEGF Trap in Patients with Neovascular Age-Related Macular Degeneration" ARVO Annual Meeting Abstract (May 2006).
Regeneron SEC Form 10-K (Feb. 27, 2008).
Regeneron SEC Form 10-K (Feb. 26, 2009).
Regeneron SEC Form 10-K (Feb. 17, 2011).
Regeneron SEC Form 10-Q (May 8, 2006).
Regeneron SEC Form 10-Q (Aug. 8, 2006).
Regeneron SEC Form 10-Q (Nov. 6, 2006).
Regeneron SEC Form 10-Q (May 4, 2007).
Regeneron SEC Form 10-Q (Aug. 3, 2007).
Regeneron SEC Form 10-Q (Apr. 30, 2009).
Regeneron SEC Form 10-Q (Nov. 3, 2009).
Regeneron SEC Form 10-Q (Apr. 29, 2010).
Regeneron SEC Form 10-Q (Jul. 28, 2010).
Regeneron SEC Form 10-Q (Oct. 28, 2010).
Regeneron SEC Form 10-Q (May 3, 2011).
Regeneron SEC Form 10-Q (Jul. 28, 2011).
Regeneron SEC Form 10-Q (Oct. 27, 2011).
Regeneron SEC Form 8-K Exhibit: "Press Release of Regeneron Pharmaceuticals, Inc. dated May 1, 2006" (May 2, 2006).
Regeneron SEC Form 8-K Exhibit: "Press Release of Regeneron Pharmaceuticals, Inc. dated May 3, 2006" (May 5, 2006).
Regeneron SEC Form 8-K Exhibit: "Slides presented at the Company's 2006 Annual Meeting of Shareholders held on Jun. 9, 2006" (Jun. 9, 2006).
Regeneron SEC Form 8-K Exhibit: "Press Release dated May 2, 2007" (May 3, 2007).
Regeneron SEC Form 8-K Exhibit: "Overheads for presentation at Regeneron's Annual Meeting of Shareholders to be held on Jun. 8, 2007" (Jun. 8, 2007).
Regeneron SEC Form 8-K Exhibit: "Press Release dated Oct. 1, 2007" (Oct. 1, 2007).
Regeneron SEC Form 8-K Exhibit: "Press Release dated Nov. 6, 2007" (Nov. 6, 2007).

(56) References Cited

OTHER PUBLICATIONS

Regeneron SEC Form 8-K Exhibit: "Press Release dated May 1, 2008" (May 2, 2008).
Regeneron SEC Form 8-K Exhibit: "Press Release dated Nov. 4, 2008" (Nov. 4, 2008).
Regeneron SEC Form 8-K Exhibit: "99(a) Slides that Regeneron Pharmaceuticals, Inc. intends to use in conjunction with meetings with investors at the J.P. Morgan 27th Annual Healthcare Conference in San Francisco on Jan. 12-15, 2009." (Jan. 9, 2009).
Regeneron SEC Form 8-K Exhibit: "Press Release dated Apr. 30, 2009" (May 1, 2009).
Regeneron SEC Form 8-K Exhibit: "Press Release dated Nov. 3, 2009." (Nov. 4, 2009).
Regeneron SEC Form 8-K Exhibit: "Press Release Reporting Positive Results for VEGF Trap-Eye in Phase 3 Study in Central Retinal Vein Occlusion (CRVO) and in Phase 2 Study in Diabetic Macular Edema (DME) dated Dec. 20, 2010." (Dec. 20, 2010).
Regeneron SEC Form 8-K Exhibit: "Press Release dated Feb. 17, 2011" (Feb. 18, 2011).
Regeneron SEC Form 8-K Exhibit: "Press Release Reporting Positive Results for VEGF Trap-Eye in Second Phase 3 Study in Central Retinal Vein Occlusion, dated Apr. 27, 2011" (Apr. 27, 2011).
Regeneron SEC Form 8-K Exhibit: "Press Release dated May 3, 2011." (May 3, 2011).
Regeneron SEC Form 8-K Exhibit: "Press Release, dated Jun. 17, 2011, Announcing that Eylea™(aflibercept ophthalmic solution) Received Unanimous Recommendation for Approval for Treatment of Wet AMD from FDA Advisory Committee." (Jun. 21, 2011).
Regeneron SEC Form 8-K Exhibit: "Presentation entitled VEGF Trap-Eye in CRVO: 1-year Results of the Phase 3 Copernicus Study" (Aug. 22, 2011).
Regeneron SEC Form 8-K Exhibit: "Press Release Announcing FDA Approval of Eyleatm (aflibercept) Injection for the Treatment of Wet Age-Related Macular Degeneration, dated Nov. 18, 2011" (Nov. 21, 2011).
Regeneron Pharmaceuticals Inc., "CLEAR-IT-2: Interim Results of the Phase II, Randomized, Controlled Dose-and Interval-ranging Study of Repeated Intravitreal VEGF Trap Administration in Patients With Neovascular Age-related Macular Degeneration (AMD)" poster presented at the 2007 Association for Research in Vision and Ophthalmology meeting in Ft. Lauderdale, Florida (May 2007).
Regeneron Pharmaceuticals Inc., "An Exploratory Study of the Safety, Tolerability and Biological Effect of a Single Intravitreal Administration of VEGF Trap in Patients with Diabetic Macular Edema" poster presented at the 2007 Association for Research in Vision and Ophthalmology meeting in Ft. Lauderdale, Florida (May 2007).
Regeneron Pharmaceuticals Inc., "Optical Coherence Tomography Outcomes of a Phase 1, Dose-Escalation, Safety, Tolerability, and Bioactivity Study of Intravitreal VEGF Trap in Patients with Neovascular Age-Related Macular Degeneration: The CLEAR-IT 1 Study" poster presented at the 2007 Association for Research in Vision and Ophthalmology meeting in Ft. Lauderdale, Florida (May 2007).
Regeneron Pharmaceuticals Inc., " View 1 Vascular Endothelial Growth Factor (VEGF) Trap-Eye 1-Year Results: Investigation of Efficacy and Safety in Wet Age-Related Macular Degeneration (AMD) " presented at Bascom Palmer Eye Institute's Angiogenesis, Exudation and Degeneration 2011 meeting in Miami, Florida (Feb. 12, 2011).
Regeneron Pharmaceuticals Inc., " VIEW 2 Vascular Endothelial Growth Factor (VEGF) Trap-Eye 1-Year Results: Investigation of Efficacy and Safety in Wet Age-Related Macular Degeneration (AMD) " presented at Bascom Palmer Eye Institute's Angiogenesis, Exudation and Degeneration 2011 meeting in Miami, Florida (Feb. 12, 2011).
Regeneron Pharmaceuticals Inc., "VEGF Trap-Eye CLEAR-IT 2 Final Primary Endpoint Results" presented at the 2007 Retina Society Conference in Boston, Massachusetts (Sep. 30, 2007).
Regeneron 2008 Annual Report.
Regeneron 2009 Annual Report and 10-K.
Regeneron 2010 Annual Report and 10-K.
Rudge et al. "Clinical Development of VEGF Trap" In: Figg W.D., Folkman J. (eds) Angiogenesis (2008).
Schmidt-Erfurth et al. "Primary Results of an International Phase III Study Using Intravitreal VEGF Trap-Eye Compared to Ranibizumab in Patients with Wet AMD (VIEW 2)" ARVO Annual Meeting Abstract (Apr. 2011).
Slakter et al., "Influence of Baseline Angiographic Classification on Outcomes in the CLEAR-IT 2 Phase 2 Study of Intravitreal VEGF Trap-Eye in Neovascular Age-Related Macular Degeneration" ARVO Annual Meeting Abstract (Apr. 2010).
Slakter et al., "A Phase 2, Randomized, Controlled Dose-and Interval-Ranging Study of Intravitreal VEGF Trap-Eye in Patients with Neovascular Age-Related Macular Degeneration: Optical Coherence Tomography (OCT) and Fluorescein Angiography (FA) Outcomes at 1 Year" ARVO Annual Meeting Abstract (Apr. 2009).
Bayer Investor News, "VEGF Trap-Eye: New Data Confirm Successes in the Treatment of Age-related Macular Degeneration" (Sep. 28, 2008).
Regeneron Press Release "Positive Interim Phase 2 Data Reported for VEGF Trap-Eye in Age-Related Macular Degeneration" (Mar. 27, 2007).
Regeneron Press Release "VEGF Trap-Eye Phase 2 Wet AMD Results Reported At ARVO Annual Meeting" (May 9, 2007).
Regeneron Press Release "Regeneron Reports Second Quarter Financial and Operating Results" (Aug. 1, 2007).
Regeneron Pharmaceuticals, Inc., "Regeneron and Bayer Healthcare Initiate Phase 3 Global Development Program for VEGF Trap-Eye in Wet Age-Related Macular Degeneration (AMD)" (Aug. 2, 2007).
Regeneron Press Release "Regeneron Announces Positive Primary Endpoint Results From A Phase 2 Study of VEGF Trap-Eye in Age-Related Macular Degeneration" (Oct. 1, 2007).
Regeneron Press Release "Regeneron Reports Fourth Quarter and Full Year 2007 Financial and Operating Results" (Feb. 27, 2008).
Regeneron Pharmaceuticals, Inc., "Regeneron and Bayer HealthCare Announce Encouraging 32-Week Follow-up Results from A Phase 2 Study of VEGF Trap-Eye in Age-Related Macular Degeneration" (Apr. 28, 2008).
Regeneron Pharmaceuticals, Inc., "Regeneron and Bayer HealthCare Announce VEGF Trap-Eye Achieved Durable Improvement in Vision over 52 Weeks in a Phase 2 Study in Patients with Age-related Macular Degeneration" (Aug. 19, 2008).
Regeneron Pharmaceuticals, Inc. "Regeneron Reports Full Year and Fourth Quarter 2008 Financial and Operating Results" (Feb. 26, 2009).
Regeneron Pharmaceuticals, Inc. "Bayer and Regeneron Extend Development Program for VEGF Trap-Eye to Include Central Retinal Vein Occlusion" (Apr. 30, 2009).
Regeneron Press Release "First Patient Enrolled in Regeneron and Bayer Healthcare VEGF Trap-Eye Phase 3 Program in Central Retinal Vein Occlusion" (Jul. 23, 2009).
Regeneron Press Release "Regeneron Schedules Nov. 22, 2010 Teleconference and Webcast to Discuss Results of Two Phase 3 Studies With VEGF Trap-Eye in Wet Age-Related Macular Degeneration" (Nov. 19, 2010).
Regeneron Press Release "Regeneron and Bayer Start Phase 3 Trial to Extend Ophthalmology Research & Development Program for VEGF Trap-Eye in Asia" (Jan. 18, 2011).
Regeneron Press Release "Regeneron to Webcast Investor Briefing on VEGF Trap-Eye Clinical Program on Sunday, Feb. 13th At 9 Am Et" (Feb. 9, 2011).
Regeneron Press Release "Regeneron Submits Biologics License Application to FDA for VEGF Trap-Eye for Treatment of Wet Age-Related Macular Degeneration" (Feb. 22, 2011).
Regeneron Press Release "Regeneron and Bayer Announce Start of Phase 3 Clinical Program in Diabetic Macular Edema" (Apr. 8, 2011).
Regeneron Pharmaceuticals, Inc., "FDA Grants Priority Review for VEGF Trap-Eye for the Treatment of Wet Age-Related Macular Degeneration" (Apr. 18, 2011).
Regeneron Press Release "VEGF Trap-Eye Submitted for EU Marketing Authorization for Treatment of Wet Age-Related Macular Degeneration (Jun. 7, 2011)".

(56) References Cited

OTHER PUBLICATIONS

Regeneron Pharmaceuticals, Inc., "Regeneron Announces EYLEA™(aflibercept ophthalmic solution) Receives Unanimous Recommendation for Approval for Treatment of Wet AMD from FDA Advisory Committee" (Jun. 17, 2011).
Regeneron Press Release "Regeneron Announces Clinical Presentations at ASRS 2011 Annual Meeting" (Aug. 17, 2011).
Regeneron Pharmaceuticals, Inc., Regeneron Announces FDA Approval of EYLEA™ (aflibercept) Injection for the Treatment of Wet Age-Related Macular Degeneration: CORRECTED (Nov. 18, 2011).
Regeneron Pharmaceuticals, Inc., "Regeneron and Bayer Initiate Phase 3 Clinical Program for the Treatment of Wet Age-Related Macular Degeneration in China" (Nov. 28, 2011).
Regeneron Pharmaceuticals, Inc., "Two Year Results of Phase 3 Studies with EYLEA™(aflibercept) Injection in wet AMD Show Sustained Improvement in Visual Acuity" (Dec. 5, 2011).
James A. Dixon et al., Expert Opin. Investig. Drugs (2009) 18(10):1573-1580.†
Regeneron Press Release dated Sep. 14, 2009.†

† cited by third party

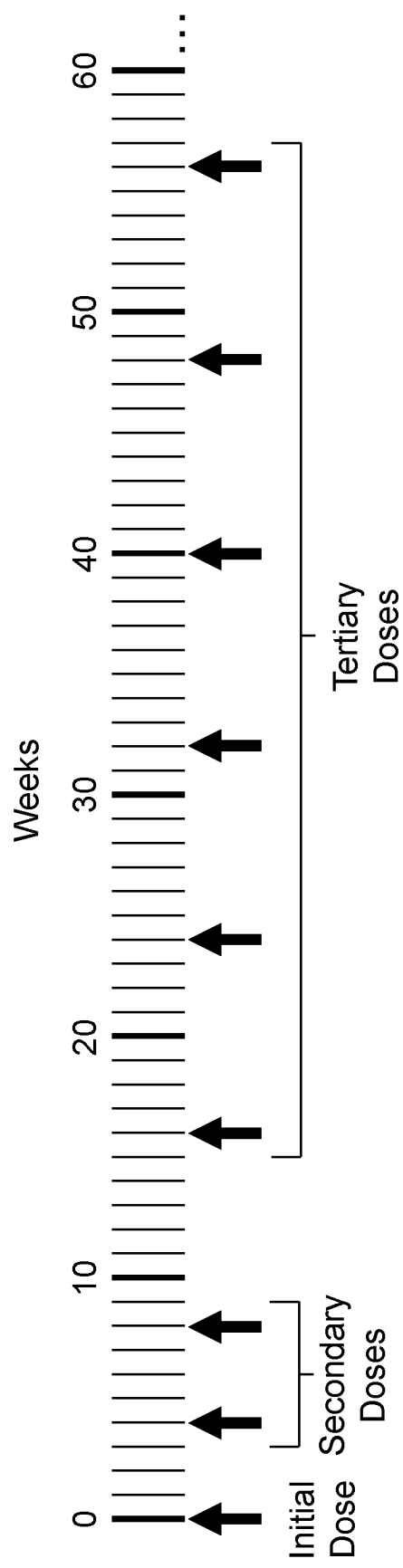

SEQUENCE LISTING

<160> NUMBER OF SEQ ID NOS: 2

<210> SEQ ID NO 1
<211> LENGTH: 1377
<212> TYPE: DNA
<213> ORGANISM: Artificial Sequence
<220> FEATURE:
<223> OTHER INFORMATION: Synthetic

<400> SEQUENCE: 1
atggtcagct actgggacac cggggtcctg ctgtgcgcgc tgctcagctg tctgcttctc     60

```
acaggatcta gttccggaag tgataccggt agacctttcg tagagatgta cagtgaaatc    120
cccgaaatta tacacatgac tgaaggaagg gagctcgtca ttccctgccg ggttacgtca    180
cctaacatca ctgttacttt aaaaaagttt ccacttgaca ctttgatccc tgatggaaaa    240
cgcataatct gggacagtag aaagggcttc atcatatcaa atgcaacgta caaagaaata    300
gggcttctga cctgtgaagc aacagtcaat gggcatttgt ataagacaaa ctatctcaca    360
catcgacaaa ccaatacaat catagatgtg gttctgagtc cgtctcatgg aattgaacta    420
tctgttggag aaaagcttgt cttaaattgt acagcaagaa ctgaactaaa tgtggggatt    480
gacttcaact gggaataccc ttcttcgaag catcagcata agaaacttgt aaaccgagac    540
ctaaaaaccc agtctgggag tgagatgaag aaattttttga gcaccttaac tatagatggt    600
gtaacccgga gtgaccaagg attgtacacc tgtgcagcat ccagtgggct gatgaccaag    660
aagaacagca catttgtcag ggtccatgaa aaggacaaaa ctcacacatg cccaccgtgc    720
ccagcacctg aactcctggg gggaccgtca gtcttcctct tccccccaaa acccaaggac    780
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta acagcacg taccgtgtgg tcagcgtcct caccgtcctg    960
caccaggact ggctgaatgg caaggagtac aagtgcaagg tctccaacaa agccctccca    1020
gcccccatcg agaaaaccat ctccaaagcc aagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga       1377
```

<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu

```
              130                 135                 140
Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
                180                 185                 190

Leu Ser Thr Leu Thr Ile Asp Gly Val Thr Arg Ser Asp Gln Gly Leu
                195                 200                 205

Tyr Thr Cys Ala Ala Ser Ser Gly Leu Met Thr Lys Lys Asn Ser Thr
        210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
                275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
                355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly Lys
450                 455
```

USE OF A VEGF ANTAGONIST TO TREAT ANGIOGENIC EYE DISORDERS

CROSS-REFERENCE TO RELATED APPLICATIONS

This application is a continuation of U.S. patent application Ser. No. 15/471,506 filed Mar. 28, 2017, now U.S. Pat. No. 10,130,681 issued Nov. 20, 2018, which is a continuation of U.S. patent application Ser. No. 14/972,560 filed Dec. 17, 2015, now U.S. Pat. No. 9,669,069 issued Jun. 6, 2017, which is a continuation of U.S. patent application Ser. No. 13/940,370 filed Jul. 12, 2013, now U.S. Pat. No. 9,254,338 issued Feb. 9, 2016, which is a continuation-in-part of International Patent Application No. PCT/US2012/020855, filed on Jan. 11, 2012, which claims the benefit of U.S. Provisional Application No. 61/432,245, filed on Jan. 13, 2011, 61/434,836, filed on Jan. 21, 2011, and 61/561,957, filed on Nov. 21, 2011, the contents of which are hereby incorporated by reference in their entireties.

FIELD OF THE INVENTION

The present invention relates to the field of therapeutic treatments of eye disorders. More specifically, the invention relates to the administration of VEGF antagonists to treat eye disorders caused by or associated with angiogenesis.

BACKGROUND

Several eye disorders are associated with pathological angiogenesis. For example, the development of age-related macular degeneration (AMD) is associated with a process called choroidal neovascularization (CNV). Leakage from the CNV causes macular edema and collection of fluid beneath the macula resulting in vision loss. Diabetic macular edema (DME) is another eye disorder with an angiogenic component. DME is the most prevalent cause of moderate vision loss in patients with diabetes and is a common complication of diabetic retinopathy, a disease affecting the blood vessels of the retina. Clinically significant DME occurs when fluid leaks into the center of the macula, the light-sensitive part of the retina responsible for sharp, direct vision. Fluid in the macula can cause severe vision loss or blindness. Yet another eye disorder associated with abnormal angiogenesis is central retinal vein occlusion (CRVO). CRVO is caused by obstruction of the central retinal vein that leads to a back-up of blood and fluid in the retina. The retina can also become ischemic, resulting in the growth of new, inappropriate blood vessels that can cause further vision loss and more serious complications. Release of vascular endothelial growth factor (VEGF) contributes to increased vascular permeability in the eye and inappropriate new vessel growth. Thus, inhibiting the angiogenic-promoting properties of VEGF appears to be an effective strategy for treating angiogenic eye disorders.

FDA-approved treatments of angiogenic eye disorders such as AMD and CRVO include the administration of an anti-VEGF antibody called ranibizumab (Lucentis®, Genentech, Inc.) on a monthly basis by intravitreal injection.

Methods for treating eye disorders using VEGF antagonists are mentioned in, e.g., U.S. Pat. Nos. 7,303,746; 7,306,799; 7,300,563; 7,303,748; and US 2007/0190058. Nonetheless, there remains a need in the art for new administration regimens for angiogenic eye disorders, especially those which allow for less frequent dosing while maintaining a high level of efficacy.

BRIEF SUMMARY OF THE INVENTION

The present invention provides methods for treating angiogenic eye disorders. The methods of the invention comprise sequentially administering multiple doses of a VEGF antagonist to a patient over time. In particular, the methods of the invention comprise sequentially administering to the patient a single initial dose of a VEGF antagonist, followed by one or more secondary doses of the VEGF antagonist, followed by one or more tertiary doses of the VEGF antagonists. The present inventors have surprisingly discovered that beneficial therapeutic effects can be achieved in patients suffering from angiogenic eye disorders by administering a VEGF antagonist to a patient at a frequency of once every 8 or more weeks, especially when such doses are preceded by about three doses administered to the patient at a frequency of about 2 to 4 weeks. Thus, according to the methods of the present invention, each secondary dose of VEGF antagonist is administered 2 to 4 weeks after the immediately preceding dose, and each tertiary dose is administered at least 8 weeks after the immediately preceding dose. An example of a dosing regimen of the present invention is shown in FIG. 1. One advantage of such a dosing regimen is that, for most of the course of treatment (i.e., the tertiary doses), it allows for less frequent dosing (e.g., once every 8 weeks) compared to prior administration regimens for angiogenic eye disorders which require monthly administrations throughout the entire course of treatment. (See, e.g., prescribing information for Lucentis® [ranibizumab], Genentech, Inc.).

The methods of the present invention can be used to treat any angiogenic eye disorder, including, e.g., age related macular degeneration, diabetic retinopathy, diabetic macular edema, central retinal vein occlusion, corneal neovascularization, etc.

The methods of the present invention comprise administering any VEGF antagonist to the patient. In one embodiment, the VEGF antagonist comprises one or more VEGF receptor-based chimeric molecule(s), (also referred to herein as a "VEGF-Trap" or "VEGFT"). An exemplary VEGF antagonist that can be used in the context of the present invention is a multimeric VEGF-binding protein comprising two or more VEGF receptor-based chimeric molecules referred to herein as "VEGFR1R2-FcΔC1(a)" or "aflibercept."

Various administration routes are contemplated for use in the methods of the present invention, including, e.g., topical administration or intraocular administration (e.g., intravitreal administration).

Aflibercept (EYLEA™, Regeneron Pharmaceuticals, Inc) was approved by the FDA in November 2011, for the treatment of patients with neovascular (wet) age-related macular degeneration, with a recommended dose of 2 mg administered by intravitreal injection every 4 weeks for the first three months, followed by 2 mg administered by intravitreal injection once every 8 weeks.

Other embodiments of the present invention will become apparent from a review of the ensuing detailed description.

BRIEF DESCRIPTION OF THE FIGURE

FIG. 1 shows an exemplary dosing regimen of the present invention. In this regimen, a single "initial dose" of VEGF antagonist ("VEGFT") is administered at the beginning of the treatment regimen (i.e. at "week 0"), two "secondary doses" are administered at weeks 4 and 8, respectively, and at least six "tertiary doses" are administered once every 8 weeks thereafter, i.e., at weeks 16, 24, 32, 40, 48, 56, etc.).

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described.

Dosing Regimens

The present invention provides methods for treating angiogenic eye disorders. The methods of the invention comprise sequentially administering to a patient multiple doses of a VEGF antagonist. As used herein, "sequentially administering" means that each dose of VEGF antagonist is administered to the patient at a different point in time, e.g., on different days separated by a predetermined interval (e.g., hours, days, weeks or months). The present invention includes methods which comprise sequentially administering to the patient a single initial dose of a VEGF antagonist, followed by one or more secondary doses of the VEGF antagonist, followed by one or more tertiary doses of the VEGF antagonist.

The terms "initial dose," "secondary doses," and "tertiary doses," refer to the temporal sequence of administration of the VEGF antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of VEGF antagonist, but will generally differ from one another in terms of frequency of administration. In certain embodiments, however, the amount of VEGF antagonist contained in the initial, secondary and/or tertiary doses will vary from one another (e.g., adjusted up or down as appropriate) during the course of treatment.

In one exemplary embodiment of the present invention, each secondary dose is administered 2 to 4 (e.g., 2, 2½, 3, 3½, or 4) weeks after the immediately preceding dose, and each tertiary dose is administered at least 8 (e.g., 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of VEGF antagonist which is administered to a patient prior to the administration of the very next dose in the sequence with no intervening doses.

In one exemplary embodiment of the present invention, a single initial dose of a VEGF antagonist is administered to a patient on the first day of the treatment regimen (i.e., at week 0), followed by two secondary doses, each administered four weeks after the immediately preceding dose (i.e., at week 4 and at week 8), followed by at least 5 tertiary doses, each administered eight weeks after the immediately preceding dose (i.e., at weeks 16, 24, 32, 40 and 48). The tertiary doses may continue (at intervals of 8 or more weeks) indefinitely during the course of the treatment regimen. This exemplary administration regimen is depicted graphically in FIG. 1.

The methods of the invention may comprise administering to a patient any number of secondary and/or tertiary doses of a VEGF antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 4 weeks after the immediately preceding dose. Similarly, in embodiments involving multiple tertiary doses, each tertiary dose may be administered at the same frequency as the other tertiary doses. For example, each tertiary dose may be administered to the patient 8 weeks after the immediately preceding dose. Alternatively, the frequency at which the secondary and/or tertiary doses are administered to a patient can vary over the course of the treatment regimen. For example, the present invention includes methods which comprise administering to the patient a single initial dose of a VEGF antagonist, followed by one or more secondary doses of the VEGF antagonist, followed by at least 5 tertiary doses of the VEGF antagonist, wherein the first four tertiary doses are administered 8 weeks after the immediately preceding dose, and wherein each subsequent tertiary dose is administered from 8 to 12 (e.g., 8, 8½, 9, 9½, 10, 10½, 11, 11½, 12) weeks after the immediately preceding dose. The frequency of administration may also be adjusted during the course of treatment by a physician depending on the needs of the individual patient following clinical examination.

VEGF Antagonists

The methods of the present invention comprise administering to a patient a VEGF antagonist according to specified dosing regimens. As used herein, the expression "VEGF antagonist" means any molecule that blocks, reduces or interferes with the normal biological activity of VEGF.

VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies, anti-VEGF receptor antibodies, and VEGF receptor-based chimeric molecules (also referred to herein as "VEGF-Traps").

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides).

An exemplary VEGF receptor-based chimeric molecule is a molecule referred to as VEGFR1R2-FcΔC1(a) which is encoded by the nucleic acid sequence of SEQ ID NO:1. VEGFR1R2-FcΔC1(a) comprises three components: (1) a VEGFR1 component comprising amino acids 27 to 129 of SEQ ID NO:2; (2) a VEGFR2 component comprising amino acids 130 to 231 of SEQ ID NO:2; and (3) a multimerization component ("FcΔC1(a)") comprising amino acids 232 to 457 of SEQ ID NO:2 (the C-terminal amino acid of SEQ ID NO:2 [i.e., K458] may or may not be included in the VEGF antagonist used in the methods of the invention; see e.g., U.S. Pat. No. 7,396,664). Amino acids 1-26 of SEQ ID NO:2 are the signal sequence.

The VEGF antagonist used in the Examples set forth herein below is a dimeric molecule comprising two VEGFR1R2-FcΔC1(a) molecules and is referred to herein as "VEGFT." Additional VEGF receptor-based chimeric molecules which can be used in the context of the present invention are disclosed in U.S. Pat. Nos. 7,396,664, 7,303,746 and WO 00/75319.

Angiogenic Eye Disorders

The methods of the present invention can be used to treat any angiogenic eye disorder. The expression "angiogenic eye disorder," as used herein, means any disease of the eye which is caused by or associated with the growth or proliferation of blood vessels or by blood vessel leakage. Non-limiting examples of angiogenic eye disorders that are treatable using the methods of the present invention include age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, and diabetic retinopathies.

Pharmaceutical Formulations

The present invention includes methods in which the VEGF antagonist that is administered to the patient is contained within a pharmaceutical formulation. The pharmaceutical formulation may comprise the VEGF antagonist along with at least one inactive ingredient such as, e.g., a pharmaceutically acceptable carrier. Other agents may be incorporated into the pharmaceutical composition to provide improved transfer, delivery, tolerance, and the like. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the antibody is administered. A multitude of appropriate formulations can be found in the formulary known to all pharmaceutical chemists: Remington's Pharmaceutical Sciences (15th ed, Mack Publishing Company, Easton, Pa., 1975), particularly Chapter 87 by Blaug, Seymour, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in the context of the methods of the present invention, provided that the VEGF antagonist is not inactivated by the formulation and the formulation is physiologically compatible and tolerable with the route of administration. See also Powell et al. PDA (1998) J Pharm Sci Technol. 52:238-311 and the citations therein for additional information related to excipients and carriers well known to pharmaceutical chemists.

Pharmaceutical formulations useful for administration by injection in the context of the present invention may be prepared by dissolving, suspending or emulsifying a VEGF antagonist in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there may be employed, e.g., sesame oil, soybean oil, etc., which may be used in combination with a solubilizing agent such as benzyl benzoate, benzyl alcohol, etc. The injection thus prepared can be filled in an appropriate ampoule if desired.

Modes of Administration

The VEGF antagonist (or pharmaceutical formulation comprising the VEGF antagonist) may be administered to the patient by any known delivery system and/or administration method. In certain embodiments, the VEGF antagonist is administered to the patient by ocular, intraocular, intravitreal or subconjunctival injection. In other embodiments, the VEGF antagonist can be administered to the patient by topical administration, e.g., via eye drops or other liquid, gel, ointment or fluid which contains the VEGF antagonist and can be applied directly to the eye. Other possible routes of administration include, e.g., intradermal, intramuscular, intraperitoneal, intravenous, subcutaneous, intranasal, epidural, and oral.

Amount of VEGF Antagonist Administered

Each dose of VEGF antagonist administered to the patient over the course of the treatment regimen may contain the same, or substantially the same, amount of VEGF antagonist. Alternatively, the quantity of VEGF antagonist contained within the individual doses may vary over the course of the treatment regimen. For example, in certain embodiments, a first quantity of VEGF antagonist is administered in the initial dose, a second quantity of VEGF antagonist is administered in the secondary doses, and a third quantity of VEGF antagonist is administered in the tertiary doses. The present invention contemplates dosing schemes in which the quantity of VEGF antagonist contained within the individual doses increases over time (e.g., each subsequent dose contains more VEGF antagonist than the last), decreases over time (e.g., each subsequent dose contains less VEGF antagonist than the last), initially increases then decreases, initially decreases then increases, or remains the same throughout the course of the administration regimen.

The amount of VEGF antagonist administered to the patient in each dose is, in most cases, a therapeutically effective amount. As used herein, the phrase "therapeutically effective amount" means a dose of VEGF antagonist that results in a detectable improvement in one or more symptoms or indicia of an angiogenic eye disorder, or a dose of VEGF antagonist that inhibits, prevents, lessens, or delays the progression of an angiogenic eye disorder. In the case of an anti-VEGF antibody or a VEGF receptor-based chimeric molecule such as VEGFR1R2-FcΔC1(a), a therapeutically effective amount can be from about 0.05 mg to about 5 mg, e.g., about 0.05 mg, about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 1.0 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.55 mg, about 1.6 mg, about 1.65 mg, about 1.7 mg, about 1.75 mg, about 1.8 mg, about 1.85 mg, about 1.9 mg, about 2.0 mg, about 2.05 mg, about 2.1 mg, about 2.15 mg, about 2.2 mg, about 2.25 mg, about 2.3 mg, about 2.35 mg, about 2.4 mg, about 2.45 mg, about 2.5 mg, about 2.55 mg, about 2.6 mg, about 2.65 mg, about 2.7 mg, about 2.75 mg, about 2.8 mg, about 2.85 mg, about 2.9 mg, about 3.0 mg, about 3.5 mg, about 4.0 mg, about 4.5 mg, or about 5.0 mg of the antibody or receptor-based chimeric molecule.

The amount of VEGF antagonist contained within the individual doses may be expressed in terms of milligrams of antibody per kilogram of patient body weight (i.e., mg/kg). For example, the VEGF antagonist may be administered to a patient at a dose of about 0.0001 to about 10 mg/kg of patient body weight.

Treatment Population and Efficacy

The methods of the present invention are useful for treating angiogenic eye disorders in patients that have been diagnosed with or are at risk of being afflicted with an angiogenic eye disorder. Generally, the methods of the present invention demonstrate efficacy within 104 weeks of the initiation of the treatment regimen (with the initial dose administered at "week 0"), e.g., by the end of week 16, by the end of week 24, by the end of week 32, by the end of week 40, by the end of week 48, by the end of week 56, etc. In the context of methods for treating angiogenic eye disorders such as AMD, CRVO, and DME, "efficacy" means that, from the initiation of treatment, the patient exhibits a loss of 15 or fewer letters on the Early Treatment Diabetic Retinopathy Study (ETDRS) visual acuity chart. In certain embodiments, "efficacy" means a gain of one or more (e.g., 1, 2, 3, 4, 5, 6, 7, 8, 9, 10, 11 or more) letters on the ETDRS chart from the time of initiation of treatment.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary VEGF antagonist used in all Examples set forth below is a dimeric molecule having two functional VEGF binding units. Each functional binding unit is comprised of Ig domain 2 from VEGFR1 fused to Ig domain 3 from VEGFR2, which in turn is fused to the hinge region of a human IgG1 Fc domain (VEGFR1R2-FcΔC1(a); encoded by SEQ ID NO:1). This VEGF antagonist is referred to in the examples below as "VEGFT". For purposes of the following Examples, "monthly" dosing is equivalent to dosing once every four weeks.

Example 1: Phase I Clinical Trial of Intravitreally Administered VEGF Receptor-Based Chimeric Molecule (VEGFT) in Subjects with Neovascular AMD In this Phase I study, 21 subjects with neovascular AMD received a single intravitreal (IVT) dose of VEGFT. Five groups of three subjects each received either 0.05, 0.15, 0.5, 2 or 4 mg of VEGFT, and a sixth group of six subjects received 1 mg. No serious adverse events related to the study drug, and no identifiable intraocular inflammation was reported. Preliminary results showed that, following injection of VEGFT, a rapid decrease in foveal thickness and macular volume was observed that was maintained through 6 weeks. At Day 43 across all dose groups, mean excess retinal thickness [excess retinal thickness=(retinal thickness−179μ)] on optical coherence tomography (OCT) was reduced from 119μ to 27μ as assessed by Fast Macular Scan and from 194μ to 60μ as assessed using a single Posterior Pole scan. The mean increase in best corrected visual acuity (BCVA) was 4.75 letters, and BCVA was stable or improved in 95% of subjects. In the 2 highest dose groups (2 and 4 mg), the mean increase in BCVA was 13.5 letters, with 3 of 6 subjects demonstrating improvement of ≥3 lines.

Example 2: Phase II Clinical Trial of Repeated Doses of Intravitreally Administered VEGF Receptor-Based Chimeric Molecule (VEGFT) in Subjects with Neovascular AMD This study was a double-masked, randomized study of 3 doses (0.5, 2, and 4 mg) of VEGFT tested at 4-week and/or 12-week dosing intervals. There were 5 treatment arms in this study, as follows: 1) 0.5 mg every 4 weeks, 2) 0.5 mg every 12 weeks, 3) 2 mg every 4 weeks, 4) 2 mg every 12 weeks and 5) 4 mg every 12 weeks. Subjects were dosed at a fixed interval for the first 12 weeks, after which they were evaluated every 4 weeks for 9 months, during which additional doses were administered based on pre-specified criteria. All subjects were then followed for one year after their last dose of VEGFT. Preliminary data from a pre-planned interim analysis indicated that VEGFT met its primary endpoint of a statistically significant reduction in retinal thickness after 12 weeks compared with baseline (all groups combined, decrease of 135μ, p<0.0001). Mean change from baseline in visual acuity, a key secondary endpoint of the study, also demonstrated statistically significant improvement (all groups combined, increase of 5.9 letters, p<0.0001). Moreover, patients in the dose groups that received only a single dose, on average, demonstrated a decrease in excess retinal thickness (p<0.0001) and an increase in visual acuity (p=0.012) at 12 weeks. There were no drug-related serious adverse events, and treatment with the VEGF antagonists was generally well-tolerated. The most common adverse events were those typically associated with intravitreal injections.

Example 3: Phase I Clinical Trial of Systemically Administered VEGF Receptor-Based Chimeric Molecule (VEGFT) in Subjects with Neovascular AMD This study was a placebo-controlled, sequential-group, dose-escalating safety, tolerability and bioeffect study of VEGFT by IV infusion in subjects with neovascular AMD. Groups of 8 subjects meeting eligibility criteria for subfoveal choroidal neovascularization (CNV) related to AMD were assigned to receive 4 IV injections of VEGFT or placebo at dose levels of 0.3, 1, or 3 mg/kg over an 8-week period.

Most adverse events that were attributed to VEGFT were mild to moderate in severity, but 2 of 5 subjects treated with 3 mg/kg experienced dose-limiting toxicity (DLT) (one with Grade 4 hypertension and one with Grade 2 proteinuria); therefore, all subjects in the 3 mg/kg dose group did not enter the study. The mean percent changes in excess retinal thickness were: −12%, −10%, −66%, and −60% for the placebo, 0.3, 1, and 3 mg/kg dose groups at day 15 (ANOVA p<0.02), and −5.6%, +47.1%, and −63.3% for the placebo, 0.3, and 1 mg/kg dose groups at day 71 (ANOVA p<0.02). There was a numerical improvement in BCVA in the subjects treated with VEGFT. As would be expected in such a small study, the results were not statistically significant.

Example 4: Phase III Clinical Trials of the Efficacy, Safety, and Tolerability of Repeated Doses of Intravitreal VEGFT in Subjects with Neovascular Age-Related Macular Degeneration A. Objectives, Hypotheses and Endpoints Two parallel Phase III clinical trials were carried out to investigate the use of VEGFT to treat patients with the neovascular form of age-related macular degeneration (Study 1 and Study 2). The primary objective of these studies was to assess the efficacy of IVT administered VEGFT compared to ranibizumab (Lucentis®, Genentech, Inc.), in a non-inferiority paradigm, in preventing moderate vision loss in subjects with all subtypes of neovascular AMD.

The secondary objectives were (a) to assess the safety and tolerability of repeated IVT administration of VEGFT in subjects with all sub-types of neovascular AMD for periods up to 2 years; and (b) to assess the effect of repeated IVT administration of VEGFT on Vision-Related Quality of Life (QOL) in subjects with all sub-types of neovascular AMD.

The primary hypothesis of these studies was that the proportion of subjects treated with VEGFT with stable or improved BCVA (<15 letters lost) is similar to the proportion treated with ranibizumab who have stable or improved BCVA, thereby demonstrating non-inferiority.

The primary endpoint for these studies was the prevention of vision loss of greater than or equal to 15 letters on the ETDRS chart, compared to baseline, at 52 weeks. Secondary endpoints were as follows: (a) change from baseline to Week 52 in letter score on the ETDRS chart; (b) gain from baseline to Week 52 of 15 letters or more on the ETDRS chart; (c) change from baseline to Week 52 in total NEI VFQ-25 score; and (d) change from baseline to Week 52 in CNV area.

B. Study Design

For each study, subjects were randomly assigned in a 1:1:1:1 ratio to 1 of 4 dosing regimens: (1) 2 mg VEGFT administered every 4 weeks (2Q4); (2) 0.5 mg VEGFT administered every 4 weeks (0.5Q4); (3) 2 mg VEGFT administered every 4 weeks to week 8 and then every 8 weeks (with sham injection at the interim 4-week visits when study drug was not administered (2Q8); and (4) 0.5 mg ranibizumab administered every 4 weeks (RQ4). Subjects assigned to (2Q8) received the 2 mg injection every 4 weeks to week 8 and then a sham injection at interim 4-week visits (when study drug is not to be administered) during the first 52 weeks of the studies. (No sham injection were given at Week 52).

The study duration for each subject was scheduled to be 96 weeks plus the recruitment period. For the first 52 weeks (Year 1), subjects received an IVT or sham injection in the study eye every 4 weeks. (No sham injections were given at Week 52). During the second year of the study, subjects will be evaluated every 4 weeks and will receive IVT injection of study drug at intervals determined by specific dosing criteria, but at least every 12 weeks. (During the second year of the study, sham injections will not be given.) During this period, injections may be given as frequently as every 4 weeks, but no less frequently than every 12 weeks, according to the following criteria: (i) increase in central retinal thickness of ≥100 μm compared to the lowest previous value as measured by optical coherence tomography (OCT); or (ii) a loss from the best previous letter score of at least 5 ETDRS letters in conjunction with recurrent fluid as indicated by OCT; or (iii) new or persistent fluid as indicated by OCT; or (iv) new onset classic neovascularization, or new or persistent leak on fluorescein angiography (FA); or (v) new macular hemorrhage; or (vi) 12 weeks have elapsed since the previous injection. According to the present protocol, subjects must receive an injection at least every 12 weeks.

Subjects were evaluated at 4 weeks intervals for safety and best corrected visual acuity (BCVA) using the 4 meter ETDRS protocol. Quality of Life (QOL) was evaluated using the NEI VFQ-25 questionnaire. OCT and FA examinations were conducted periodically.

Approximately 1200 subjects were enrolled, with a target enrollment of 300 subjects per treatment arm.

To be eligible for this study, subjects were required to have subfoveal choroidal neovascularization (CNV) secondary to AMD. "Subfoveal" CNV was defined as the presence of subfoveal neovascularization, documented by FA, or presence of a lesion that is juxtafoveal in location angiographically but affects the fovea. Subject eligibility was confirmed based on angiographic criteria prior to randomization.

Only one eye was designated as the study eye. For subjects who met eligibility criteria in both eyes, the eye with the worse VA was selected as the study eye. If both eyes had equal VA, the eye with the clearest lens and ocular media and least amount of subfoveal scar or geographic atrophy was selected. If there was no objective basis for selecting the study eye, factors such as ocular dominance, other ocular pathology and subject preference were considered in making the selection.

Inclusion criteria for both studies were as follows: (i) signed Informed consent; (ii) at least 50 years of age; (iii) active primary subfoveal CNV lesions secondary to AMD, including juxtafoveal lesions that affect the fovea as evidenced by FA in the study eye; (iv) CNV at least 50% of total lesion size; (v) early treatment diabetic retinopathy study (ETDRS) best-corrected visual acuity of: 20/40 to 20/320 (letter score of 73 to 25) in the study eye; (vi) willing, committed, and able to return for all clinic visits and complete all study-related procedures; and (vii) able to read, understand and willing to sign the informed consent form (or, if unable to read due to visual impairment, be read to verbatim by the person administering the informed consent or a family member).

Exclusion criteria for both studies were as follows: 1. Any prior ocular (in the study eye) or systemic treatment or surgery for neovascular AMD except dietary supplements or vitamins. 2. Any prior or concomitant therapy with another investigational agent to treat neovascular AMD in the study eye, except dietary supplements or vitamins. 3. Prior treatment with anti-VEGF agents as follows: (a) Prior treatment with anti-VEGF therapy in the study eye was not allowed; (b) Prior treatment with anti-VEGF therapy in the fellow eye with an investigational agent (not FDA approved, e.g. bevacizumab) was allowed up to 3 months prior to first dose in the study, and such treatments were not allowed during the study. Prior treatment with an approved anti-VEGF therapy in the fellow eye was allowed; (c) Prior systemic anti-VEGF therapy, investigational or FDA/Health Canada approved, was only allowed up to 3 months prior to first dose, and was not allowed during the study. 4. Total lesion size>12 disc areas (30.5 mm2, including blood, scars and neovascularization) as assessed by FA in the study eye. 5. Subretinal hemorrhage that is either 50% or more of the total lesion area, or if the blood is under the fovea and is 1 or more disc areas in size in the study eye. (If the blood is under the fovea, then the fovea must be surrounded 270 degrees by visible CNV.) 6. Scar or fibrosis, making up>50% of total lesion in the study eye. 7. Scar, fibrosis, or atrophy involving the center of the fovea. 8. Presence of retinal pigment epithelial tears or rips involving the macula in the study eye. 9. History of any vitreous hemorrhage within 4 weeks prior to Visit 1 in the study eye. 10. Presence of other causes of CNV, including pathologic myopia (spherical equivalent of −8 diopters or more negative, or axial length of 25 mm or more), ocular histoplasmosis syndrome, angioid streaks, choroidal rupture, or multifocal choroiditis in the study eye. 11. History or clinical evidence of diabetic retinopathy, diabetic macular edema or any other vascular disease affecting the retina, other than AMD, in either eye. 12. Prior vitrectomy in the study eye. 13. History of retinal detachment or treatment or surgery for retinal detachment in the study eye. 14. Any history of macular hole of stage 2 and above in the study eye. 15. Any intraocular or periocular surgery within 3 months of Day 1 on the study eye, except lid surgery, which may not have taken place within 1 month of day 1, as long as it was unlikely to interfere with the injection. 16. Prior trabeculectomy or other filtration surgery in the study eye. 17. Uncontrolled glaucoma (defined as intraocular pressure greater than or equal to 25 mm Hg despite treatment with anti-glaucoma medication) in the study eye. 18. Active intraocular inflammation in either eye. 19. Active ocular or periocular infection in either eye. 20. Any ocular or periocular infection within the last 2 weeks prior to Screening in either eye. 21. Any history of uveitis in either eye. 22. Active scleritis or episcleritis in either eye. 23. Presence or history of scleromalacia in either eye. 24. Aphakia or pseudophakia with absence of posterior capsule (unless it occurred as a result of a yttrium aluminum garnet [YAG] posterior capsulotomy) in the study eye. 25. Previous therapeutic radiation in the region of the study eye. 26. History of corneal transplant or corneal dystrophy in the study eye. 27. Significant media opacities, including cataract, in the study eye which might interfere with visual acuity, assessment of safety, or fundus photography. 28. Any concurrent intraocular condition in the study eye (e.g. cataract) that, in the opinion of the investigator, could require either medical or surgical intervention during the 96 week study period. 29. Any concurrent ocular condition in the study eye which, in the opinion of the investigator, could either increase the risk to the subject beyond what is to be expected from standard procedures of intraocular injection, or which otherwise may interfere with the injection procedure or with evaluation of efficacy or safety. 30. History of other disease, metabolic dysfunction, physical examination finding, or clinical laboratory finding giving reasonable suspicion of a disease or condition that contraindicates the use of an investigational drug or that might affect interpretation of the results of the study or render the subject at high risk for treatment complications. 31. Participation as a subject in any clinical study within the 12 weeks prior to Day 1. 32. Any systemic or ocular treatment with an investigational agent in the past 3 months prior to Day 1. 33. The use of long acting steroids, either systemically or intraocularly, in the 6 months prior to day 1. 34. Any history of allergy to povidone iodine. 35. Known serious allergy to the fluorescein sodium for injection in angiography. 36. Presence of any contraindications indicated in the FDA Approved label for ranibizumab (Lucentis®). 37. Females who were pregnant, breastfeeding, or of childbearing potential, unwilling to practice adequate contraception throughout the study. Adequate contraceptive measures include oral contraceptives (stable use for 2 or more cycles prior to screening); IUD; Depo-Provera®; Norplant® System implants; bilateral tubal ligation; vasectomy; condom or diaphragm plus either contraceptive sponge, foam or jelly.

Subjects were not allowed to receive any standard or investigational agents for treatment of their AMD in the study eye other than their assigned study treatment with VEGFT or ranibizumab as specified in the protocol until they completed the Completion/Early Termination visit assessments. This includes medications administered locally (e.g., IVT, topical, juxtascleral or periorbital routes), as well as those administered systemically with the intent of treating the study and/or fellow eye.

The study procedures are summarized as follows:

Best Corrected Visual Acuity:

Visual function of the study eye and the fellow eye were assessed using the ETDRS protocol (The Early Treatment Diabetic Retinopathy Study Group) at 4 meters. Visual Acuity examiners were certified to ensure consistent measurement of BCVA. The VA examiners were required to remain masked to treatment assignment.

Optical Coherence Tomography:

Retinal and lesion characteristics were evaluated using OCT on the study eye. At the Screen Visit (Visit 1) images were captured and transmitted for both eyes. All OCT images were captured using the Zeiss Stratus OCT™ with software Version 3 or greater. OCT images were sent to an independent reading center where images were read by masked readers at visits where OCTs were required. All OCTs were electronically archived at the site as part of the source documentation. A subset of OCT images were read. OCT technicians were required to be certified by the reading center to ensure consistency and quality in image acquisition. Adequate efforts were made to ensure that OCT technicians at the site remained masked to treatment assignment.

Fundus Photography and Fluorescein Angiography (FA):

The anatomical state of the retinal vasculature of the study eye was evaluated by funduscopic examination, fundus photography and FA. At the Screen Visit (Visit 1) funduscopic examination, fundus photography and FA were captured and transmitted for both eyes. Fundus and angiographic images were sent to an independent reading center where images were read by masked readers. The reading center confirmed subject eligibility based on angiographic criteria prior to randomization. All FAs and fundus photographs were archived at the site as part of the source documentation. Photographers were required to be certified by the reading center to ensure consistency and quality in image acquisition. Adequate efforts were made to ensure that all photographers at the site remain masked to treatment assignment.

Vision-Related Quality of Life:

Vision-related QOL was assessed using the National Eye Institute 25-Item Visual Function Questionnaire (NEI VFQ-25) in the interviewer-administered format. NEI VFQ-25 was administered by certified personnel at a contracted call center. At the screening visit, the sites assisted the subject and initiated the first call to the call center to collect all of the subject's contact information and to complete the first NEI VFQ-25 on the phone prior to randomization and IVT injection. For all subsequent visits, the call center called the subject on the phone, prior to IVT injection, to complete the questionnaire.

Intraocular Pressure:

Intraocular pressure (IOP) of the study eye was measured using applanation tonometry or Tonopen. The same method of IOP measurement was used in each subject throughout the study.

C. Results Summary (52 Week Data)

The primary endpoint (prevention of moderate or severe vision loss as defined above) was met for all three VEGFT groups (2Q4, 0.5Q4 and 2Q8) in this study. The results from both studies are summarized in Table 1.

TABLE 1

|  | Ranibizumab 0.5 mg monthly (RQ4) | VEGFT 0.5 mg monthly (0.5Q4) | VEGFT 2 mg monthly (2Q4) | VEGFT 2 mg every 8 weeks[a] (2Q8) |
|---|---|---|---|---|
| Maintenance of vision* (% patients losing <15 letters) at week 52 versus baseline ||||
| Study 1 | 94.4% | 95.9%** | 95.1%** | 95.1%** |
| Study 2 | 94.4% | 96.3%** | 95.6%** | 95.6%** |
| Mean improvement in vision* (letters) at 52 weeks versus baseline (p-value vs RQ4)*** ||||
| Study 1 | 8.1 | 6.9 (NS) | 10.9 (p < 0.01) | 7.9 (NS) |
| Study 2 | 9.4 | 9.7 (NS) | 7.6 (NS) | 8.9 (NS |

[a]Following three initial monthly doses
*Visual acuity was measured as the total number of letters read correctly on the Early Treatment Diabetic Retinopathy Study (ETDRS) eye chart.
**Statistically non-inferior based on a non-inferiority margin of 10%, using confidence interval approach (95.1% and 95% for Study 1 and Study 2, respectively)
***Test for superiority
NS = non-significant In Study 1, patients receiving VEGFT 2 mg monthly (2Q4) achieved a statistically significant greater mean improvement in visual acuity at week 52 versus baseline (secondary endpoint), compared to ranibizumab 0.5 mg monthly (RQ4); patients receiving VEGFT 2 mg monthly on average gained 10.9 letters, compared to a mean 8.1 letter gain with ranibizumab 0.5 mg dosed every month (p<0.01). All other dose groups of VEGFT in Study 1 and all dose groups in Study 2 were not statistically different from ranibizumab in this secondary endpoint.

A generally favorable safety profile was observed for both VEGFT and ranibizumab. The incidence of ocular treatment emergent adverse events was balanced across all four treatment groups in both studies, with the most frequent events associated with the injection procedure, the underlying disease, and/or the aging process. The most frequent ocular adverse events were conjunctival hemorrhage, macular degeneration, eye pain, retinal hemorrhage, and vitreous floaters. The most frequent serious non-ocular adverse events were typical of those reported in this elderly population who receive intravitreal treatment for wet AMD; the most frequently reported events were falls, pneumonia, myocardial infarction, atrial fibrillation, breast cancer, and acute coronary syndrome. There were no notable differences among the study arms.

Example 5: Phase II Clinical Trial of VEGFT in Subjects with Diabetic Macular Edema (DME)

In this study, 221 patients with clinically significant DME with central macular involvement were randomized, and 219 patients were treated with balanced distribution over five groups. The control group received macular laser therapy at baseline, and patients were eligible for repeat laser treatments, but no more frequently than at 16 week intervals. The remaining four groups received VEGFT by intravitreal injection as follows: Two groups received 0.5 or 2 mg of VEGFT once every four weeks throughout the 12-month dosing period (0.5Q4 and 2Q4, respectively). Two groups received three initial doses of 2 mg VEGFT once every four weeks (i.e., at baseline, and weeks 4 and 8), followed through week 52 by either once every 8 weeks dosing (2Q8) or as needed dosing with very strict repeat dosing criteria (PRN). Mean gains in visual acuity versus baseline were as shown in Table 2:

TABLE 2

|  | n | Mean change in visual acuity at week 24 versus baseline (letters) | Mean change in visual acuity at week 52 versus baseline (letters) |
|---|---|---|---|
| Laser | 44 | 2.5 | −1.3 |
| VEGFT 0.5 mg monthly (0.5Q4) | 44 | 8.6** | 11.0** |
| VEGFT 2 mg monthly (2Q4) | 44 | 11.4** | 13.1** |
| VEGFT 2 mg every 8 weeks[a] (2Q8) | 42 | 8.5** | 9.7** |
| VEGFT 2 mg as needed[a] (PRN) | 45 | 10.3** | 12.0** |

[a]Following three initial monthly doses
**p < 0.01 versus laser

In this study, the visual acuity gains achieved with VEGFT administration at week 24 were maintained or numerically improved up to completion of the study at week 52 in all VEGFT study groups, including 2 mg dosed every other month As demonstrated in the foregoing Examples, the administration of VEGFT to patients suffering from angiogenic eye disorders (e.g., AMD and DME) at a frequency of once every 8 weeks, following a single initial dose and two secondary doses administered four weeks apart, resulted in significant prevention of moderate or severe vision loss or improvements in visual acuity.

Example 6: A Randomized, Multicenter, Double-Masked Trial in Treatment Naïve Patients with Macular Edema Secondary to CRVO In this randomized, double-masked, Phase 3 study, patients received 6 monthly injections of either 2 mg intravitreal VEGFT (114 patients) or sham injections (73 patients). From Week 24 to Week 52, all patients received 2 mg VEGFT as-needed (PRN) according to retreatment criteria. Thus, "sham-treated patients" means patients who received sham injections once every four weeks from Week 0 through Week 20, followed by intravitreal VEGFT as needed from Week 24 through Week 52. "VEGFT-treated patients" means patients who received VEGFT intravitreal injections once every four weeks from Week 0 through Week 20, followed by intravitreal VEGFT as needed from Week 24 through Week 52. The primary endpoint was the proportion of patients who gained ≤15 ETDRS letters from baseline at Week 24. Secondary visual, anatomic, and Quality of Life NEI VFQ-25 outcomes at Weeks 24 and 52 were also evaluated.

At Week 24, 56.1% of VEGFT-treated patients gained ≤15 ETDRS letters from baseline vs 12.3% of sham-treated patients (P<0.0001). Similarly, at Week 52, 55.3% of VEGFT-treated patients gained ≤15 letters vs 30.1% of sham-treated patients (P<0.01). At Week 52, VEGFT-treated patients gained a mean of 16.2 letters vs 3.8 letters for sham-treated patients (P<0.001). Mean number of injections was 2.7 for VEGFT-treated patients vs 3.9 for sham-treated patients. Mean change in central retinal thickness was −413.0 μm for VEGFT-treated patients vs −381.8 μm for sham-treated patients. The proportion of patients with ocular neovascularization at Week 24 were 0% for VEGFT-treated patients and 6.8% for sham-treated patients, respectively; at Week 52 after receiving VEGFT PRN, proportions were 0% and 6.8% for VEGFT-treated and sham-treated. At Week 24, the mean change from baseline in the VFQ-25 total score was 7.2 vs 0.7 for the VEGFT-treated and sham-treated groups; at Week 52, the scores were 7.5 vs 5.1 for the VEGFT-treated and sham-treated groups.

This Example confirms that dosing monthly with 2 mg intravitreal VEGFT injection resulted in a statistically significant improvement in visual acuity at Week 24 that was maintained through Week 52 with PRN dosing compared with sham PRN treatment. VEGFT was generally well tolerated and had a generally favorable safety profile.

Example 7: Dosing Regimens

Specific, non-limiting examples of dosing regimens within the scope of the present invention are as follows:

VEGFT 2 mg (0.05 mL) administered by intravitreal injection once every 4 weeks (monthly).

VEGFT 2 mg (0.5 mL) administered by intravitreal injection once every 4 weeks for the first 8 weeks, followed by 2 mg (0.05 mL) via intravitreal injection once every 8 weeks.

VEGFT 2 mg (0.5 mL) administered by intravitreal injection once every 4 weeks for the first 8 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 8 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 12 weeks, followed by 2 mg (0.05 mL) via intravitreal injection once every 8 weeks.

VEGFT 2 mg (0.5 mL) administered by intravitreal injection once every 4 weeks for the first 12 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 12 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 16 weeks, followed by 2 mg (0.05 mL) via intravitreal injection once every 8 weeks.

VEGFT 2 mg (0.5 mL) administered by intravitreal injection once every 4 weeks for the first 16 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 16 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 20 weeks, followed by 2 mg (0.05 mL) via intravitreal injection once every 8 weeks.

VEGFT 2 mg (0.5 mL) administered by intravitreal injection once every 4 weeks for the first 20 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 20 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 24 weeks, followed by 2 mg (0.05 mL) via intravitreal injection once every 8 weeks.

VEGFT 2 mg (0.5 mL) administered by intravitreal injection once every 4 weeks for the first 24 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 24 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 28 weeks, followed by 2 mg (0.05 mL) via intravitreal injection once every 8 weeks.

VEGFT 2 mg (0.5 mL) administered by intravitreal injection once every 4 weeks for the first 28 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 28 weeks, followed by 2 mg (0.05 mL) via intravitreal injection administered pro re nata (PRN) based on visual and/or anatomical outcomes (as assessed by a physician or other qualified medical professional).

VEGFT 2 mg (0.05 mL) administered by intravitreal injection as a single initial dose, followed by additional doses administered pro re nata (PRN) based on visual and/or anatomical outcomes (as assessed by a physician or other qualified medical professional).

Variations on the above-described dosing regimens would be appreciated by persons of ordinary skill in the art and are also within the scope of the present invention. For example, the amount of VEGFT and/or volume of formulation administered to a patient may be varied based on patient characteristics, severity of disease, and other diagnostic assessments by a physician or other qualified medical professional.

Any of the foregoing administration regimens may be used for the treatment of, e.g., age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, etc.

SEQUENCES
(DNA sequence having 1377 nucleotides):
SEQ ID NO: 1
ATGGTCAGCTACTGGGACACCGGGGTCCTGCTGTGCGCGCTGCTCAGCTG

TCTGCTTCTCACAGGATCTAGTTCCGGAAGTGATACCGGTAGACCTTTCG

TAGAGATGTACAGTGAAATCCCCGAAATTATACACATGACTGAAGGAAGG

GAGCTCGTCATTCCCTGCCGGGTTACGTCACCTAACATCACTGTTACTTT

AAAAAAGTTTCCACTTGACACTTTGATCCCTGATGGAAAACGCATAATCT

GGGACAGTAGAAAGGGCTTCATCATATCAAATGCAACGTACAAAGAAATA

GGGCTTCTGACCTGTGAAGCAACAGTCAATGGGCATTTGTATAAGACAAA

CTATCTCACACATCGACAAACCAATACAATCATAGATGTGGTTCTGAGTC

CGTCTCATGGAATTGAACTATCTGTTGGAGAAAAGCTTGTCTTAAATTGT

ACAGCAAGAACTGAACTAAATGTGGGGATTGACTTCAACTGGGAATACCC

TTCTTCGAAGCATCAGCATAAGAAACTTGTAAACCGAGACCTAAAAACCC

AGTCTGGGAGTGAGATGAAGAAATTTTTGAGCACCTTAACTATAGATGGT

GTAACCCGGAGTGACCAAGGATTGTACACCTGTGCAGCATCCAGTGGGCT

GATGACCAAGAAGAACAGCACATTTGTCAGGGTCCATGAAAAGGACAAAA

CTCACACATGCCCACCGTGCCCAGCACCTGAACTCCTGGGGGGACCGTCA

GTCTTCCTCTTCCCCCCAAAACCCAAGGACACCCTCATGATCTCCCGGAC

CCCTGAGGTCACATGCGTGGTGGTGGACGTGAGCCACGAAGACCCTGAGG

TCAAGTTCAACTGGTACGTGGACGGCGTGGAGGTGCATAATGCCAAGACA

AAGCCGCGGGAGGAGCAGTACAACAGCACGTACCGTGTGGTCAGCGTCCT

CACCGTCCTGCACCAGGACTGGCTGAATGGCAAGGAGTACAAGTGCAAGG

TCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCT

CTACAGCAAGCTCACCGTGGACAAGAGCAGGTGGCAGCAGGGGAACGTCT

TCTCATGCTCCGTGATGCATGAGGCTCTGCACAACCACTACACGCAGAAG

AGCCTCTCCCTGTCTCCGGGTAAATGA (polypeptide sequence having 458 amino acids):
SEQ ID NO: 2
MVSYWDTGVLLCALLSCLLLTGSSSGSDTGRPFVEMYSEIPEIIHMTEGR

ELVIPCRVTSPNITVTLKKFPLDTLIPDGKRIIWDSRKGFIISNATYKEI

GLLTCEATVNGHLYKTNYLTHRQTNTIIDVVLSPSHGIELSVGEKLVLNC

TARTELNVGIDFNWEYPSSKHQHKKLVNRDLKTQSGSEMKKFLSTLTIDG

VTRSDQGLYTCAASSGLMTKKNSTFVRVHEKDKTHTCPPCPAPELLGGPS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPGK

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating an angiogenic eye disorder in a patient, said method comprising sequentially administering to the patient a single initial dose of a VEGF antagonist, followed by one or more secondary doses of the VEGF antagonist, followed by one or more tertiary doses of the VEGF antagonist;
    wherein each secondary dose is administered 4 weeks after the immediately preceding dose; and wherein each tertiary dose is administered 12 weeks after the immediately preceding dose;
    wherein the VEGF antagonist is a receptor-based chimeric molecule comprising an immunoglobin-like (Ig) domain 2 of a first VEGF receptor which is Flt1 and Ig domain 3 of a second VEGF receptor which is Flk1, and a multimerizing component.

2. The method of claim 1, wherein the VEGF antagonist is aflibercept.

3. The method of claim 1, wherein all doses of the VEGF antagonist are administered to the patient by intraocular administration.

4. The method of claim 3, wherein the intraocular administration is intravitreal administration.

5. The method of claim 4, wherein all doses of the VEGF antagonist comprise from about 0.5 mg to about 2 mg of the VEGF antagonist.

6. The method of claim 5, wherein all doses of the VEGF antagonist comprise 0.5 mg of the VEGF antagonist.

7. The method of claim 5, wherein all doses of the VEGF antagonist comprise 2 mg of the VEGF antagonist.

8. The method of claim 5, wherein the angiogenic eye disorder is selected from the group consisting of: age related macular degeneration, diabetic retinopathy, diabetic macular edema, central retinal vein occlusion, branch retinal vein occlusion, and corneal neovascularization.

9. The method of claim 8 wherein the angiogenic eye disorder is age related macular degeneration.

10. The method of claim 8 wherein the angiogenic eye disorder is diabetic retinopathy.

11. The method of claim 8, wherein the angiogenic eye disorder is diabetic macular edema.

\* \* \* \* \*

UNITED STATES PATENT AND TRADEMARK OFFICE
CERTIFICATE OF CORRECTION

PATENT NO. : 10,828,345 B2
APPLICATION NO. : 16/159282
DATED : November 10, 2020
INVENTOR(S) : Yancopoulos It is certified that error appears in the above-identified patent and that said Letters Patent is hereby corrected as shown below:

In the Specification

At Column 15, Line 5, please correct from "gained $\leq$15 ETDRS" to read --gained $\geq$15 ETDRS--.

At Column 15, Lines 9-10, please correct from "gained $\leq$15 ETDRS" to read --gained $\geq$15 ETDRS--.

At Column 15, Line 12, please correct from "gained $\leq$15 letters" to read --gained $\geq$15 letters--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*